(12) United States Patent
Walch

(10) Patent No.: US 12,279,829 B2
(45) Date of Patent: Apr. 22, 2025

(54) METHODS, SYSTEMS AND DEVICES FOR PRE-OPERATIVELY PLANNED GLENOID PLACEMENT GUIDES AND USES THEREOF

(71) Applicant: Stryker European Operations Limited, Carrigtwohill (IE)

(72) Inventor: Gilles Walch, Lyons (FR)

(73) Assignee: Stryker European Operations Limited, Carrigtwohill (IE)

( * ) Notice: Subject to any disclaimer, the term of this patent is extended or adjusted under 35 U.S.C. 154(b) by 0 days.

(21) Appl. No.: 18/217,175

(22) Filed: Jun. 30, 2023

(65) Prior Publication Data
US 2023/0346480 A1    Nov. 2, 2023

Related U.S. Application Data

(63) Continuation of application No. 17/117,546, filed on Dec. 10, 2020, now Pat. No. 11,712,302, which is a
(Continued)

(51) Int. Cl.
*A61B 17/56* (2006.01)
*A61B 17/16* (2006.01)
(Continued)

(52) U.S. Cl.
CPC .......... *A61B 34/10* (2016.02); *A61B 17/1684* (2013.01); *A61B 17/1739* (2013.01);
(Continued)

(58) Field of Classification Search
CPC ........ A61B 2017/568; A61B 2034/105; A61B 2034/108; A61B 34/10; A61B 17/1684;
(Continued)

(56) References Cited

U.S. PATENT DOCUMENTS 5,768,134 A    6/1998 Swaellers
7,618,451 B2    11/2009 Berez et al.
(Continued)

FOREIGN PATENT DOCUMENTS

CA    3203261 A1    7/2022
EP    2670314 B1    8/2014
(Continued)

OTHER PUBLICATIONS

Boissonnat, J.D., "Shape Reconstruction from Planar Cross Sections," Computer Vision, Graphics, and Image Processing, vol. 44, No. 1, Oct. 1988, 29 pp.
(Continued)

*Primary Examiner* — Samuel S Hanna
(74) *Attorney, Agent, or Firm* — Shumaker & Sieffert, P.A.

(57) ABSTRACT

Methods, systems and devices for pre-operatively planned shoulder surgery guides and implants. Pre-operative planning methods for designing glenoid placement guides and depth-control pins based on considerations of multiple factors affecting the outcome of shoulder surgery. Methods of using surgery guides and implants, including glenoid placement guides and depth-control pins, in patients undergoing shoulder surgery.

10 Claims, 11 Drawing Sheets

Related U.S. Application Data continuation of application No. 15/029,879, filed as application No. PCT/IB2014/002759 on Oct. 17, 2014, now Pat. No. 10,888,378.

(60) Provisional application No. 61/892,196, filed on Oct. 17, 2013.

(51) Int. Cl.
*A61B 17/17* (2006.01)
*A61B 34/10* (2016.01)
*A61F 2/40* (2006.01)
*A61F 2/46* (2006.01)

(52) U.S. Cl.
CPC .......... *A61F 2/4081* (2013.01); *A61F 2/4657* (2013.01); *A61B 17/1778* (2016.11); *A61B 2017/568* (2013.01); *A61B 2034/105* (2016.02); *A61B 2034/108* (2016.02); *A61F 2002/4658* (2013.01); *A61F 2002/4668* (2013.01); *A61F 2002/4677* (2013.01); *A61F 2002/4687* (2013.01)

(58) Field of Classification Search
CPC ............. A61B 17/1739; A61B 17/1778; A61F 2/4657; A61F 2002/4658; A61F 2002/4677; A61F 2002/4668; A61F 2002/4687; A61F 2/4081
See application file for complete search history.

(56) References Cited

U.S. PATENT DOCUMENTS

| | | |
|---|---|---|
| 7,981,158 B2 | 7/2011 | Fitz et al. |
| 8,062,302 B2 | 11/2011 | Lang et al. |
| 8,105,330 B2 | 1/2012 | Fitz et al. |
| 8,160,345 B2 | 4/2012 | Pavlovskaia et al. |
| 8,175,683 B2 | 5/2012 | Roose |
| 8,221,430 B2 | 7/2012 | Park et al. |
| 8,337,501 B2 | 12/2012 | Fitz et al. |
| 8,444,651 B2 | 5/2013 | Kunz et al. |
| 8,480,753 B2 | 7/2013 | Collazo et al. |
| 8,532,361 B2 | 9/2013 | Pavlovskaia et al. |
| 8,535,319 B2 | 9/2013 | Ball |
| 8,545,509 B2 | 10/2013 | Park et al. |
| 8,551,169 B2 | 10/2013 | Fitz et al. |
| 8,585,708 B2 | 11/2013 | Fitz et al. |
| 8,734,455 B2 | 5/2014 | Park et al. |
| 8,777,875 B2 | 7/2014 | Park |
| 8,801,719 B2 | 8/2014 | Park et al. |
| 8,808,302 B2 | 8/2014 | Roose et al. |
| 8,864,769 B2 | 10/2014 | Stone et al. |
| 8,903,530 B2 | 12/2014 | Metzger |
| 8,986,309 B1 | 3/2015 | Murphy |
| 8,992,538 B2 | 3/2015 | Keefer |
| 9,011,456 B2 | 4/2015 | Ranawat et al. |
| 9,060,788 B2 | 6/2015 | Bollinger |
| 9,084,617 B2 | 7/2015 | Lang et al. |
| 9,107,679 B2 | 8/2015 | Lang et al. |
| 9,138,258 B2 | 9/2015 | Geebelen |
| 9,186,161 B2 | 11/2015 | Lang et al. |
| 9,198,732 B2 | 12/2015 | Iannotti et al. |
| 9,204,977 B2 | 12/2015 | Bollinger |
| 9,220,516 B2 | 12/2015 | Lang et al. |
| 9,232,955 B2 | 1/2016 | Bonin, Jr. et al. |
| 9,289,221 B2 | 3/2016 | Gelaude et al. |
| 9,295,482 B2 | 3/2016 | Fitz et al. |
| 9,326,780 B2 | 5/2016 | Wong et al. |
| 9,351,743 B2 | 5/2016 | Kehres et al. |
| 9,381,026 B2 | 7/2016 | Trouilloud et al. |
| 9,386,994 B2 | 7/2016 | Agnihotri et al. |
| 9,421,021 B2 | 8/2016 | Keppler |
| 9,451,973 B2 | 9/2016 | Heilman et al. |
| 9,498,233 B2 | 11/2016 | Eash |
| 9,579,106 B2 | 2/2017 | Lo et al. |
| 9,579,110 B2 | 2/2017 | Bojarski et al. |
| 9,597,201 B2 | 3/2017 | Bollinger |
| 9,615,834 B2 | 4/2017 | Agnihotri et al. |
| 9,615,840 B2 | 4/2017 | Iannotti et al. |
| 9,693,785 B2 | 7/2017 | Theiss et al. |
| 9,717,508 B2 | 8/2017 | Iannotti et al. |
| 9,757,238 B2 | 9/2017 | Metzger |
| 9,763,682 B2 | 9/2017 | Bettenga |
| 9,795,393 B2 | 10/2017 | Hughes et al. |
| 9,808,261 B2 | 11/2017 | Gelaude et al. |
| 9,820,868 B2 | 11/2017 | Witt et al. |
| 9,839,438 B2 | 12/2017 | Eash |
| 9,936,962 B2 | 4/2018 | Heilman et al. |
| 9,987,024 B2 | 6/2018 | Frey et al. |
| 10,010,334 B2 | 7/2018 | Keppler |
| 10,010,431 B2 | 7/2018 | Eraly et al. |
| 10,022,137 B2 | 7/2018 | Theiss et al. |
| 10,052,114 B2 | 8/2018 | Keppler et al. |
| 10,092,419 B2 | 10/2018 | Hananouchi et al. |
| 10,130,378 B2 | 11/2018 | Bryan |
| 10,206,688 B2 | 2/2019 | Park et al. |
| 10,349,953 B2 | 7/2019 | Park et al. |
| 10,405,993 B2 | 9/2019 | Deransart et al. |
| 10,426,493 B2 | 10/2019 | Kehres et al. |
| 10,426,549 B2 | 10/2019 | Kehres et al. |
| 10,441,298 B2 | 10/2019 | Eash |
| 10,543,100 B2 | 1/2020 | Couture et al. |
| 10,624,655 B2 | 4/2020 | Iannotti et al. |
| 10,736,697 B2 | 8/2020 | Chaoui et al. |
| 10,762,623 B2 | 9/2020 | Geebelen et al. |
| 10,842,510 B2 | 11/2020 | Heilman et al. |
| 10,842,512 B2 | 11/2020 | Bonin, Jr. et al. |
| 10,888,378 B2 | 1/2021 | Walch |
| 10,912,571 B2 | 2/2021 | Pavlovskaia et al. |
| 10,925,658 B2 | 2/2021 | Hopkins |
| 11,039,889 B2 | 6/2021 | Frey et al. |
| 11,071,592 B2 | 7/2021 | McGuan et al. |
| 11,129,678 B2 | 9/2021 | Park |
| 11,134,963 B2 | 10/2021 | Buza et al. |
| 11,166,733 B2 | 11/2021 | Neichel et al. |
| 11,179,249 B2 | 11/2021 | Deransart et al. |
| 11,213,305 B2 | 1/2022 | Iannotti et al. |
| 11,234,721 B2 | 2/2022 | Gargac et al. |
| 11,278,299 B2 | 3/2022 | Neichel et al. |
| 11,298,140 B2 | 4/2022 | Wilkinson et al. |
| 11,298,142 B2 | 4/2022 | Park et al. |
| 11,298,188 B2 | 4/2022 | Kehres et al. |
| 11,399,851 B2 | 8/2022 | Neichel et al. |
| 11,399,894 B2 | 8/2022 | Chaoui et al. |
| 11,419,618 B2 | 8/2022 | Kehres et al. |
| 11,432,934 B2 | 9/2022 | Couture et al. |
| 11,471,303 B2 | 10/2022 | O'Grady |
| 11,602,360 B2 | 3/2023 | Heilman et al. |
| 11,617,591 B2 | 4/2023 | Eash |
| 11,712,302 B2 | 8/2023 | Walch |
| 11,730,497 B2 | 8/2023 | Iannotti et al. |
| 11,766,336 B2 | 9/2023 | Penninger et al. |
| 2004/0138754 A1 | 7/2004 | Lang et al. |
| 2004/0236424 A1 | 11/2004 | Berez et al. |
| 2006/0079963 A1 | 4/2006 | Hansen |
| 2007/0233141 A1 | 10/2007 | Park et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2009/0216285 A1 | 8/2009 | Ek et al. |
| 2010/0023015 A1 | 1/2010 | Park |
| 2010/0082035 A1 | 4/2010 | Keefer |
| 2010/0160917 A1 | 6/2010 | Fitz et al. |
| 2010/0222781 A1 | 9/2010 | Collazo et al. |
| 2010/0305573 A1 | 12/2010 | Fitz et al. |
| 2010/0305574 A1 | 12/2010 | Fitz et al. |
| 2011/0029088 A1 | 2/2011 | Rausher et al. |
| 2011/0152869 A1 | 6/2011 | Ek |
| 2011/0190775 A1 | 8/2011 | Ure |
| 2011/0295329 A1 | 12/2011 | Fitz et al. |
| 2012/0101503 A1 | 4/2012 | Lang et al. |

(56) References Cited

U.S. PATENT DOCUMENTS

| | | |
|---|---|---|
| 2012/0143267 A1* | 6/2012 | Iannotti .............. A61B 17/1746 606/86 R |
| 2012/0245647 A1 | 9/2012 | Kunz et al. |
| 2012/0276509 A1* | 11/2012 | Iannotti .............. A61B 17/1739 434/267 |
| 2012/0289965 A1 | 11/2012 | Gelaude et al. |
| 2012/0303035 A1 | 11/2012 | Geebelen |
| 2013/0018378 A1 | 1/2013 | Hananouchi et al. |
| 2013/0110116 A1 | 5/2013 | Kehres |
| 2013/0172898 A1 | 7/2013 | Iannotti et al. |
| 2013/0245631 A1 | 9/2013 | Bettenga |
| 2013/0338673 A1 | 12/2013 | Keppler |
| 2014/0142578 A1 | 5/2014 | Hananouchi et al. |
| 2014/0163564 A1 | 6/2014 | Bollinger |
| 2015/0112348 A1 | 4/2015 | Schoenefeld et al. |
| 2015/0223941 A1* | 8/2015 | Lang ................. A61B 17/1778 606/87 |
| 2016/0157937 A1 | 6/2016 | Kehres et al. |
| 2016/0192951 A1 | 7/2016 | Gelaude et al. |
| 2017/0150978 A1 | 6/2017 | Iannotti et al. |
| 2018/0014835 A1 | 1/2018 | Lo et al. |
| 2018/0235642 A1 | 8/2018 | Amis et al. |
| 2019/0015118 A1 | 1/2019 | Neichel et al. |
| 2019/0015221 A1 | 1/2019 | Neichel et al. |
| 2019/0069913 A1 | 3/2019 | Iannotti et al. |
| 2019/0201005 A1 | 7/2019 | Schoenefeld et al. |
| 2019/0269415 A1 | 9/2019 | Lo et al. |
| 2020/0155323 A1 | 5/2020 | Lang et al. |
| 2020/0330161 A1 | 10/2020 | Chaoui et al. |
| 2020/0405330 A1 | 12/2020 | Bonin, Jr. et al. |
| 2021/0068844 A1 | 3/2021 | Lo et al. |
| 2021/0128179 A1 | 5/2021 | Dupuis et al. |
| 2021/0259844 A1 | 8/2021 | Penninger et al. |
| 2021/0386435 A1 | 12/2021 | Buza et al. |
| 2022/0022895 A1 | 1/2022 | Neichel et al. |
| 2022/0031475 A1 | 2/2022 | Deransart et al. |
| 2022/0047278 A1 | 2/2022 | Fitz et al. |
| 2022/0160405 A1 | 5/2022 | Casey et al. |
| 2022/0296259 A1 | 9/2022 | Shah |
| 2022/0330957 A1 | 10/2022 | Neichel et al. |
| 2023/0000645 A1 | 1/2023 | O'Grady |
| 2023/0061695 A1 | 3/2023 | Couture et al. |
| 2023/0109478 A1 | 4/2023 | Chaoui et al. |
| 2023/0329791 A1 | 10/2023 | Chaoui et al. |

FOREIGN PATENT DOCUMENTS

| | | |
|---|---|---|
| EP | 2244654 B1 | 3/2017 |
| EP | 2770920 B1 | 7/2017 |
| EP | 3248553 A1 | 11/2017 |
| EP | 3760142 A1 | 1/2021 |
| EP | 3845154 A1 | 7/2021 |
| WO | 2011142998 A1 | 11/2011 |
| WO | 2013060851 A1 | 5/2013 |
| WO | 2013142998 A1 | 10/2013 |
| WO | 2015018921 A1 | 2/2015 |
| WO | 2015052586 A2 | 4/2015 |
| WO | 2015071757 A1 | 5/2015 |
| WO | 2021026029 A1 | 2/2021 |
| WO | 2022147591 A1 | 7/2022 |

OTHER PUBLICATIONS

First Examination Report from counterpart Australian Application No. 2021201702 dated Dec. 1, 2021, 2 pp.

First Examination Report issued in connection with corresponding Australian Patent Application No. 2019236696, Jun. 18, 2020, 4 pages.

International Search Report and Written Opinion of the International Searching Authority issued for PCT Application No. PCT/IB2014/002759 mailed Mar. 27, 2015, 13 pp.

Marker et al., "Contour-Based Surface Reconstruction using Implicit Curve Fitting, and Distance Field Filtering and Interpolation," Volume Graphics, Jan. 2006, 9 pp.

Nguyen et al., "A new segmentation method for MRI images of the shoulder joint," Fourth Canadian Conference on Computer and Robot Vision (CRV'07), May 2007, 8 pp.

Notice of Acceptance from counterpart Australian Application No. 2021201702 dated Apr. 1, 2022, 3 pp.

Notice of Allowance from counterpart Canadian Application No. 2,927,811 dated Jan. 18, 2022, 1 pp.

Office Action from counterpart Canadian Application No. 2,927,811, dated Apr. 29, 2021, 3 pp.

Office Action from counterpart Canadian Application No. 2,927,811, dated Nov. 17, 2020, 3 pp.

Office Action issued in connection with corresponding Canadian Patent Application No. 2,927,811, May 25, 2020, 3 pp.

Prosecution History from U.S. Appl. No. 15/029,879, dated May 17, 2018 through Dec. 16, 2020, 122 pp.

Prosecution History from U.S. Appl. No. 17/117,546, dated Dec. 10, 2020 through Mar. 14, 2023, 29 pp.

Response to Office Action dated Dec. 1, 2021, from counterpart Australian Application No. 2021201702 filed Mar. 30, 2022, 1 pp.

Response to Official Action from counterpart Canadian Application No. 2,927,811, dated Apr. 29, 2021, filed Aug. 26, 2021, 8 pp.

Response to Official Action from counterpart Canadian Application No. 2,927,811, dated May 25, 2020, filed Sep. 25, 2020, 19 pp.

Response to Official Action from counterpart Canadian Application No. 2,927,811, dated Nov. 17, 2020, filed Mar. 16, 2021, 15 pp.

Response to Official Action from counterpart Canadian Application No. 2,927,811, dated Oct. 10, 2019, filed Apr. 14, 2020, 11 pp.

Nguyen et al., "Design and Development of a Computer Assisted Glenoid Implantation Technique for Shoulder Replacement Surgery," Computer Aided Surgery, vol. 12, No. 3, May 2007, pp. 152-159.

Raaijmaakers et al., "A Custom-Made Guide-Wire Positioning Device for Hip Surface Replacement Arthroplasty: Description and First Results," BMC Musculoskeletal Disorders, vol. 11, Jul. 2010, 7 pp.

* cited by examiner

METHODS, SYSTEMS AND DEVICES FOR PRE-OPERATIVELY PLANNED GLENOID PLACEMENT GUIDES AND USES THEREOF

CROSS REFERENCE TO RELATED APPLICATIONS

This application is a continuation of U.S. patent application Ser. No. 17/117,546, filed on Dec. 10, 2020, which is a continuation of U.S. patent application Ser. No. 15/029,879, filed on Apr. 15, 2016, which is a National Stage Application, filed under 35 U.S.C. 371, of International Patent Application No. PCT/IB2014/002759, filed on Oct. 17, 2014, which claims the benefit of U.S. Provisional Patent Application Ser. No. 61/892,196, filed Oct. 17, 2013, the disclosures of which are incorporated herein by reference in their entireties.

TECHNICAL FIELD

The presently disclosed subject matter relates to methods, systems and devices for pre-operatively planned glenoid placement guides. The presently disclosed subject matter also relates to the use of such glenoid placement guides in patients undergoing shoulder surgery.

BACKGROUND

Shoulder replacement is a common surgical operation that has achieved positive results for many patients. Indeed, approximately 10% of joint replacement procedures globally are related to the shoulder. Many shoulder procedures are performed in a patient where substantially normally bone exists for orientation and fixation of a prosthetic replacement, or resurfacing. In these cases, the need for the shoulder replacement can often times be related mostly to the arthritic condition of the joint, and relative absence of healthy cartilage.

In some patients, however, one or more of the bones of the shoulder are not only arthritic, but have also had previous conditions that have caused bone to wear away. In such cases, there may not be sufficient bone to adequately affix a prosthetic implant to the bone, or the bones may have been worn such that the orientation of a joint replacement cannot be satisfactorily determined to ensure a positive patient outcome.

There are a number of factors that complicate the selection, orientation and affixation of prosthetic implant devices, such as glenoid implants and/or humeral implants. Failure to properly account for each factor can lead to improperly sized, misaligned and/or poorly affixed implants that result in a poor surgical outcome for the patient.

In order to increase the likelihood of successful patient outcomes in patients undergoing shoulder surgery, methods, systems and devices are needed that allow for the full understanding and incorporation of all necessary factors for optimization of shoulder implant selection and placement. Thus, a need remains for methods, systems and devices for pre-operatively planned shoulder surgery guides and implants that achieve desired outcomes.

SUMMARY

The presently disclosed subject matter provides methods, systems and devices for pre-operatively planned glenoid placement guides. The presently disclosed subject matter also provides methods of using glenoid placement guides in patients undergoing shoulder surgery.

An object of the presently disclosed subject matter having been stated hereinabove, and which is achieved in whole or in part by the presently disclosed subject matter, other objects will become evident as the description proceeds when taken in connection with the accompanying Examples as best described hereinbelow.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

For a more complete understanding of the presently disclosed subject matter, reference is now made to the following drawings in which.

DETAILED DESCRIPTION

Figure 1A:
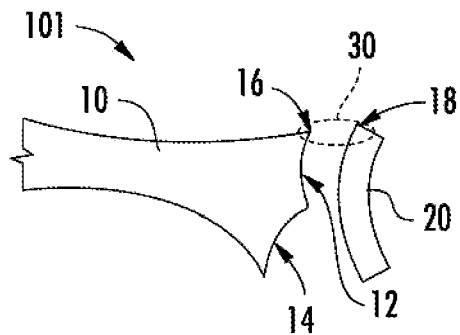
FIG. 1A is a schematic illustration of a step in a pre-operative planning method for designing a shoulder surgery guide where the anterior edge of a glenoid implant is aligned with an anterior edge of a glenoid bone, according to an embodiment of the disclosed subject matter.

Patients requiring shoulder surgery may have one or more of the bones of the shoulder that are not only arthritic, but may also have had previous conditions that have caused bone to wear away. In such cases, there may not be sufficient bone to adequately affix a prosthetic implant to the bone during a routine shoulder surgery. Indeed, the bones may have been worn such that the orientation of a joint replacement cannot be satisfactorily determined to ensure a positive patient outcome.

The glenoid bone can be subject to increased wear due to bone arthritic conditions of the joint, and due to alterations of a normal soft tissue envelope surrounding the joint. In such cases, the orientation of the face of the glenoid portion of the scapula bone may be altered so that the humeral bone is no longer appropriately apposed to the glenoid surface. In the case where the glenoid is severely worn, there can be two or more risks a surgeon must balance in an attempt to improve shoulder function and pain relief.

First, if the optimal orientation of the diseased but treated shoulder is not found and replicated with the prosthesis the patient may experience most operative complications related to subluxation or dislocation of the replaced shoulder joint. This can occur either due to passive inputs to the shoulder (e.g., leaning against it, or lying in bed), or due to active firing of surrounding soft tissue which is not able to be constrained by the replaced joint surfaces.

Additionally, the fixation of a replacement prosthesis, or implant, to the native patient bone can be problematic. Frequently, in order to counteract the risks associated with joint subluxation and dislocation described above, it can be necessary for a surgeon to orient or position the replacement prosthesis or implant in a position better suited to resist imbalanced muscle forces. In such cases, separation forces between the implant and the bone can increase, which in turn can increase the potential for loosening of the joint prosthesis in the bone. Implant loosening can be related to accelerated implant wear, bone erosion, increased tissue inflammation, joint synovitis, and pain.

In patients that have undergone shoulder replacement surgery, range of motion and strength are dependent on shoulder kinematics, which are in turn dependent on a host of factors. Such factor can, for example, include for example implant size, implant position, the design of implant shape, the joint line and soft tissue tension. In some cases it can be difficult to predict optimal implant size and position/orientation using currently available guides and implants. Often times a surgeon finds that there are too many variables to manage at one time. Moreover, the size choices of implants can be limited to the lowest practically functional groups to reduce economic burden to the health care system. Current implant designs and methodologies are inadequate to address these challenges because they are of significant cost, require time to develop, include increased risk of implant failure, and rely on human judgment of potential outcomes post-operatively.

There are many factors that can affect the optimal positioning of shoulder implants during replacement surgery. For example, such factors can include the patient size, relative bone wear, soft tissue strength and condition, six degrees-of-freedom positioning of the glenoid and/or the humeral prosthesis, selected implant size, preoperative patient activity and strength levels, post operative treatment protocols, size and density of patient bone. Additional factors can include patient smoking status, concomitant handicaps and/or patient problems. It can be quite difficult for a surgeon to understand and balance these factors simultaneously. In addition, only a few of these factors are able to be controlled by the surgeon. Finally, each factor does not necessarily have an equally weighted impact on patient outcome. Nevertheless, it is considered that the implant size, position, orientation and bone preparation of the glenoid and the humerus can have a significant impact on the surgical outcomes.

A factor that further complicates, or makes more difficult, a surgeons task of optimally placing a replacement component or implant to counteract these risk is the fact that the condition of the scapula is such that few landmarks exists for the surgeon the comprehend the implant position within the bone. Thus, frequently a surgeon might find that the implant position is not replicating as was envisioned during the surgical intervention.

Others have attempted to improve a surgeon's chance of providing successful patient outcomes by providing operative techniques and tools. What is missing, however, is the ability to fully understand and incorporate multiple factors to optimize the implant selection and placement. Specifically, in some embodiments, the success of the surgery can be highly dependent on both the selection of the matching prosthesis or prostheses (humeral and/or glenoid), as well as positioning of this prosthesis, as well as the soft tissue status before the surgery. There have been no previous attempts at including these factors in surgical planning and implant design.

Disclosed herein are methods, systems and devices for pre-operatively planned shoulder surgery guides, including glenoid placement guides, and implants. Methods, systems and devices are provided for the replacement of the shoulder joint, such as the glenohumeral joint, wherein the conditions of the humeral and soft tissue envelop is taken into consideration. More specifically, what is considered is that the shape and position of the glenoid implant is not based solely on what can be seen and measured on the scapula, but can be chosen, designed, planned and placed with incorporation of the same information related to the humerus. After all, the shoulder is a two part joint, i.e. glenoid and humeral head, wherein both parts work in conjunction with one another, and the factors that affect performance of the device can in some embodiments include factors from both sides of the joint.

Appropriate sizing of the prosthesis can be important to successful outcomes, knowing that oversized or "over-stuffed" replacement shoulders are more likely to dislocate, loosen, be painful, and/or have decreased range of motion. Replaced joints where the orientation of the prostheses is improper increases the likelihood of implant dislocation and loosening. Additionally, over-reaming, or too much bone removal, either on the glenoid, or the humerus, can be the cause of implant loosening, "under-stuffing" or inappropriate articular surface placement which can increase pain and decrease range of motion.

Provided herein in some embodiments is a glenoid implant designed and manufactured to specifically match the patient anatomy, including optimal humeral and/or glenoid implant size and shape, and taking into account one or more of the following factors: assessment of the humeral implant fit to the humeral bone; relative hardness of the patient bone preoperatively; height and diameter of the humeral head placed on the humeral stem; orientation, or "offset" of the humeral head; and optimal bone removal for preservation of soft tissue insertion and attachment.

Also provided herein are methods, systems and devices for creation of a shoulder surgery guide, including glenoid placement guides, based on pre-operative planning which takes into consideration a plurality of factors and assessments. In some embodiments, the creation of a shoulder surgery guide based on pre-operative planning can comprise one or more of the following steps, the combination and order of which can vary: aligning an anterior edge of a glenoid implant with an anterior edge of a glenoid bone; adjusting a retroversion of the glenoid implant; adjusting an augmentation of the glenoid implant; adjusting an inferior tilt of the glenoid implant; evaluating bone support for the glenoid implant, wherein an amount of a rear surface of the glenoid implant that is supported by or touching bone is assessed; adjusting the medialization of the glenoid implant by assessing the volumetric amount of bone needed to be removed by reaming, or the minimum total distance of reaming necessary, in order to optimize the bone to implant interface; analyzing the fixation support in the absence of central pegs that penetrate a vault medially; analyzing the joint line, comprising comparing an original joint line and a new joint line, wherein the new joint line is substantially similar to the original joint line; measuring and matching widths of the glenoid implant and the glenoid bone after reaming and aligning inferior/superior axes of the glenoid implant and bone; assessing and adjusting as needed a thickness/height of the glenoid implant; assessing and adjusting as needed a depth of a glenoid fossa; assessing and adjusting as needed a thickness of a graft; determining a diameter of a humeral head; determining a height of the humeral head; determining a size of humeral bone implant from Houndsfield units measured by an imaging technique (e.g. computed tomography (CT) scan); and/or determining a best fit size of implant from a range of sizes, wherein the range of sizes is selected from the group consisting of length of stem, size of humeral stem, diameter of stem, size diameter of head, height of head, and offset of the center spherical head compared to the center of the face of the humeral stem.

In some embodiments, a pre-operative planning method for designing a shoulder surgery guide is provided for designing a guide for the glenoid, including a glenoid placement guide. Such a method can be separate from a pre-operative planning method for the humerus, or can in some embodiments be done in conjunction with the planning for the humerus, or humeral side of the joint. Such planning steps particular to the glenoid side of the joint can comprise analysis steps such as those depicted in FIGS. 1A-1I.

For example, a pre-operative planning method for the glenoid can comprise a step 101, as depicted in FIG. 1A, where the anterior edge 18 of glenoid implant 20 can be aligned 30 with anterior edge 16 of glenoid 12 of scapula bone 10 of a patient to be treated. In some embodiments, this step, as with other pre-operative analyses disclosed herein, can be accomplished virtually based on images, e.g. CT images or X-ray images, taken from a subject or patient prior to surgery. By aligning anterior edge 18 of glenoid implant 20 with anterior edge 16 of glenoid 12, data and information can be collected that informs the selection of a glenoid implant and/or supports the creation of a shoulder surgery guide device specific to the patient or subject to be treated.

Figure 1B:
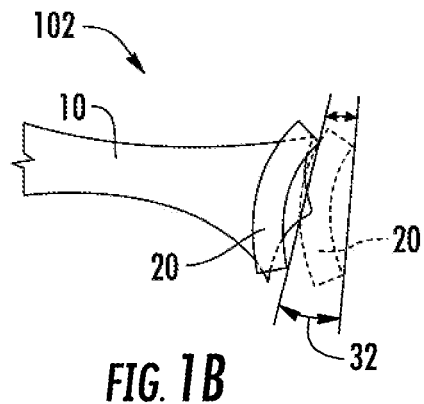
FIG. 1B is a schematic illustration of a step in a pre-operative planning method for designing a shoulder surgery guide where the retroversion of a glenoid implant is adjusted, according to an embodiment of the disclosed subject matter.

In some embodiments, a pre-operative planning method for the glenoid can comprise a step 102, as depicted in FIG. 1B, where the retroversion 32 of glenoid implant 20 is adjusted and/or measured. The retroversion is the placement or degree of posterior rotation of glenoid implant 20 when glenoid 12, including posterior wear 14 (see FIG. 1A), is reamed or otherwise resurfaced to accommodate glenoid implant 20. Such a measurement of retroversion 32 of glenoid implant 20 can be in comparison to the retroversion of the native glenoid in a subject to be treated. In some embodiments, adjusting the retroversion comprises adjusting the retroversion to be about 5 degrees (5°) to about 10 degrees (10°), with a maximum of 10°. In some embodiments, this analysis can be accomplished virtually based on images taken from a subject or patient prior to surgery. By measuring and/or adjusting the retroversion 32 of glenoid implant 20, data and information can be collected that informs the selection of a glenoid implant and/or supports the creation of a shoulder surgery guide device specific to the patient or subject to be treated.

Figure 1C:
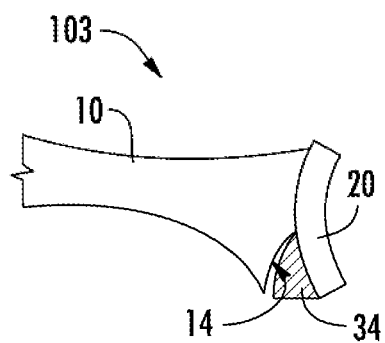
FIG. 1C is a schematic illustration of a step in a pre-operative planning method for designing a shoulder surgery guide where the augmentation of a glenoid implant is adjusted, according to an embodiment of the disclosed subject matter.

In some embodiments, a pre-operative planning method for the glenoid can comprise a step 103, as depicted in FIG. 1C, where a determination can be made as to the necessity of augmentation 34 to support glenoid implant 20. In some embodiments, particularly where glenoid 12 includes posterior wear 14 (or wear at other locations of glenoid 12 not depicted in FIG. 1C), augmentation can be necessary and/or desirable to provide adequate support for the placement and/or attachment of implant 20. Such a step or analysis can in some embodiments comprise adjusting, sizing and/or measuring augmentation 34 needed. In some embodiments, this analysis can be accomplished virtually based on images taken from a subject or patient prior to surgery. By assessing the need for augmentation 34, and/or determining the type and/or size of augmentation 34, data and information can be collected that informs the selection of a glenoid implant and/or supports the creation of a shoulder surgery guide device specific to the patient or subject to be treated.

Figure 1D:
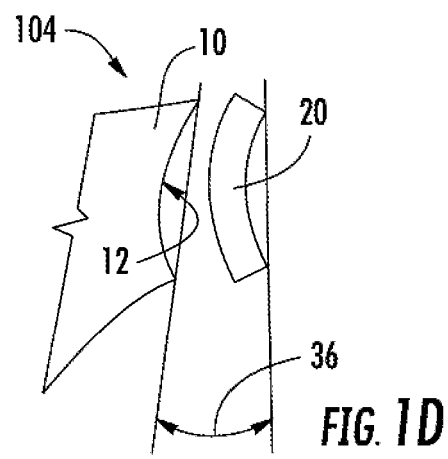
FIG. 1D is a schematic illustration of a step in a pre-operative planning method for designing a shoulder surgery guide where the inferior tilt of a glenoid implant is adjusted, according to an embodiment of the disclosed subject matter.

In some embodiments, a pre-operative planning method for the glenoid can comprise a step 104, as depicted in FIG. 1D, where the inferior tilt 36 of glenoid implant 20 can be measured and/or assessed. Such a measurement of inferior tilt 36 of glenoid implant 20 can be in comparison to the tilt of the native glenoid in a subject to be treated. In some embodiments, this analysis can be accomplished virtually based on images taken from a subject or patient prior to surgery. By assessing the inferior tilt 36 of glenoid implant 20, data and information can be collected that informs the selection of a glenoid implant and/or supports the creation of a shoulder surgery guide device specific to the patient or subject to be treated.

Figure 1E:
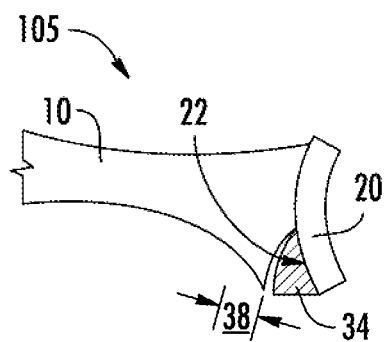
FIG. 1E is a schematic illustration of a step in a pre-operative planning method for designing a shoulder surgery guide where bone support for a glenoid implant is evaluated, according to an embodiment of the disclosed subject matter.

In some embodiments, a pre-operative planning method for the glenoid can comprise a step 105, as depicted in FIG. 1E, where the bone support 38 for glenoid implant 20 can be measured and/or assessed. Such an assessment can in some embodiments comprise characterizing and/or quantifying the amount or degree of bone support 38 for back side 22 of implant 20, taking into consideration posterior wear 14 (see, e.g., FIG. 1A or 1C; or wear at other locations of glenoid 12 not depicted). In some embodiments, this analysis can be accomplished virtually based on images taken from a subject or patient prior to surgery. By assessing the bone support 38, data and information can be collected that informs the selection of a glenoid implant and/or supports the creation of a shoulder surgery guide device specific to the patient or subject to be treated.

Figure 1F:
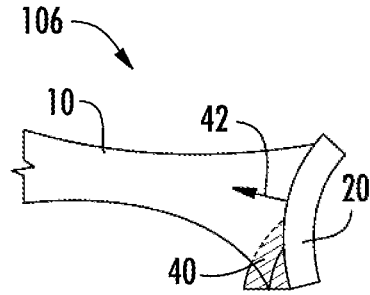
FIG. 1F is a schematic illustration of a step in a pre-operative planning method for designing a shoulder surgery guide where the medialization of a glenoid implant is adjusted by assessing the volumetric amount of bone needed to be removed by reaming, according to an embodiment of the disclosed subject matter.

In some embodiments, a pre-operative planning method for the glenoid can comprise a step 106, as depicted in FIG. 1F, where medialization 42 of glenoid implant 20 can be adjusted and/or characterized by assessing the volumetric amount 40 of bone needed to be removed by reaming. In some embodiments, this analysis can be accomplished virtually based on images taken from a subject or patient prior to surgery. By assessing the bone support 38, data and information can be collected that informs the selection of a glenoid implant and/or supports the creation of a shoulder surgery guide device specific to the patient or subject to be treated.

Figure 1G:
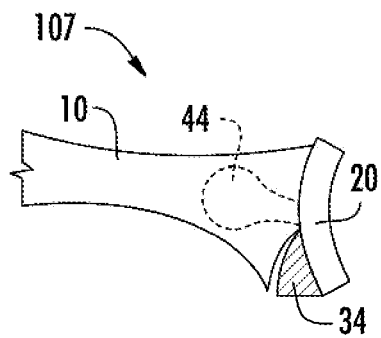
FIG. 1G is a schematic illustration of a step in a pre-operative planning method for designing a shoulder surgery guide where fixation support in the absence of central pegs that penetrate a vault medially is analyzed, according to an embodiment of the disclosed subject matter.

In some embodiments, a pre-operative planning method for the glenoid can comprise a step 107, as depicted in FIG. 1G, where fixation support in the absence of a central peg 44 that penetrates a vault medially of scapula 10 can be analyzed. In some embodiments, it is desirable to identify a location on the glenoid for attachment of a prosthesis using a peg or other fixation component without penetrating the anterior wall of the scapula. In some embodiments, this analysis can be accomplished virtually based on images taken from a subject or patient prior to surgery. By assessing the fixation support, data and information can be collected that informs the selection of a glenoid implant and/or supports the creation of a shoulder surgery guide device specific to the patient or subject to be treated.

Figure 1H:
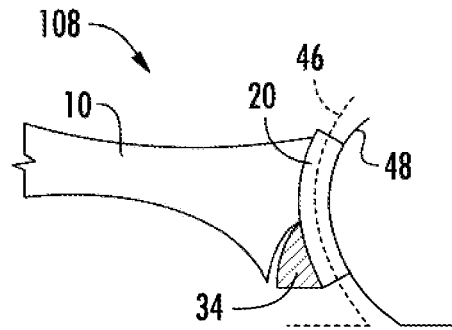
FIG. 1H is a schematic illustration of a step in a preoperative planning method for designing a shoulder surgery guide where a joint line is analyzed by comparing an original joint line and a new joint line, according to an embodiment of the disclosed subject matter.

In some embodiments, a pre-operative planning method for the glenoid can comprise a step 108, as depicted in FIG. 1H, where a joint line can be analyzed by comparing an original joint line 46 with a new joint line 48 as created when implant 20 is affixed to the glenoid surface of scapula 10. The degree to which the joint line changes or shifts, and/or the change in the angle, can be used in optimizing the implant 20 selection and/or placement. In some embodiments, analyzing the joint line, including comparing the original joint line and the new joint line, can comprise analyzing the humeral head lateralization. Humeral head lateralization can comprise the distance the humeral shaft is moved laterally relative to the scapula after the implants are placed. In some embodiments, this analysis can be accomplished virtually based on images taken from a subject or patient prior to surgery. By assessing the joint line, data and information can be collected that informs the selection of a glenoid implant and/or supports the creation of a shoulder surgery guide device specific to the patient or subject to be treated.

Figure 1I:
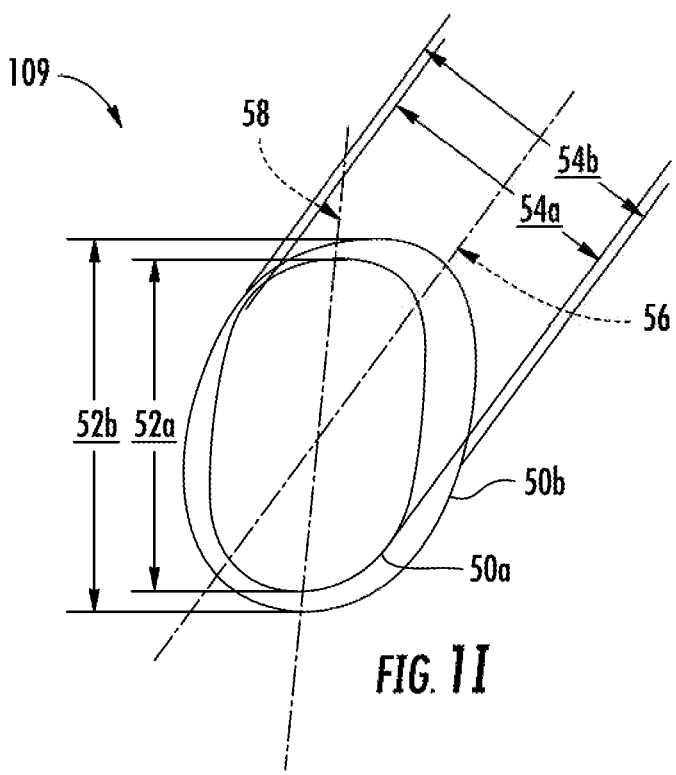
FIG. 1I is a schematic illustration of a step in a preoperative planning method for designing a shoulder surgery guide where widths of the glenoid implant and the glenoid bone are measured and matched after reaming and aligning inferior and superior axes of the glenoid implant and bone, according to an embodiment of the disclosed subject matter.

In some embodiments, a pre-operative planning method for the glenoid can comprise a step 109, as depicted in FIG. 1I, where the widths of the glenoid implant 50*a* and the glenoid bone 50*b* can be measured and matched after reaming and aligning inferior 56 and superior 58 axes of the glenoid implant and bone. Particularly, in some embodiments, a glenoid implant 50*a* height 52*a* and width 54*a* can be measured and aligned with a glenoid bone 50*b* height 52*b* and width 54*b* along inferior 56 and superior 58 axes. In some embodiments, this analysis can be accomplished virtually based on images taken from a subject or patient prior to surgery. By measuring the widths of the glenoid implant 50*a* and the glenoid bone 50*b*, and aligning inferior 56 and superior 58 axes of the glenoid implant and bone, data and information can be collected that informs the selection of a glenoid implant and/or supports the creation of a shoulder surgery guide device specific to the patient or subject to be treated.

Such planning steps particular to the glenoid side of the joint can comprise analysis steps such as those depicted in FIGS. 1A-1I, and can comprise all or some of the steps depicted in FIGS. 1A-1I, and in some aspects can be done in any order desired. Alternatively, in some embodiments analysis steps particular to fixation elements can be performed first followed by analysis steps particular to joint articulation.

In some embodiments, a pre-operative planning method for designing a shoulder surgery guide is provided for designing a guide for the humerus, or humeral bone. Such a method can be separate from a pre-operative planning method for the glenoid (discussed above and depicted in FIGS. 1a-1I), or can in some embodiments be done in conjunction with the planning for the glenoid, or glenoid side of the joint. Such planning steps particular to the humerus side of the joint can comprise analysis steps such as those depicted in FIGS. 2A-2D.

Figure 2A:
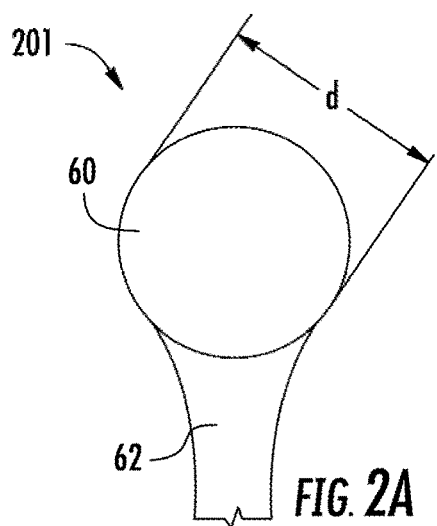
FIG. 2A is a schematic illustration of a step in a preoperative planning method for designing a shoulder surgery guide where the diameter of a humeral head is determined, according to an embodiment of the disclosed subject matter.

For example, a pre-operative planning method for the humerus can comprise a step 201, as depicted in FIG. 2A, where the diameter d of humeral head 60 of humerus 62 can be measured. In some embodiments, this analysis can be accomplished virtually based on images taken from a subject or patient prior to surgery. By measuring diameter d of humeral head 60, data and information can be collected that informs the selection of a humeral head implant and/or supports the creation of a shoulder surgery guide device specific to the patient or subject to be treated.

Figure 2B:
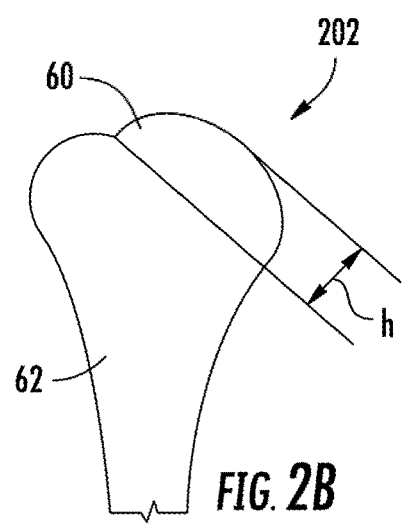
FIG. 2B is a schematic illustration of a step in a preoperative planning method for designing a shoulder surgery guide where the height of a humeral head is determined, according to an embodiment of the disclosed subject matter.

In some embodiments, a pre-operative planning method for the humerus can comprise a step 202, as depicted in FIG. 2B, where the height h of humeral head 60 of humerus 62 can be measured. In some embodiments, this analysis can be accomplished virtually based on images taken from a subject or patient prior to surgery. By measuring height h of humeral head 60, data and information can be collected that informs the selection of a humeral head implant and/or supports the creation of a shoulder surgery guide device specific to the patient or subject to be treated.

Figure 2C:
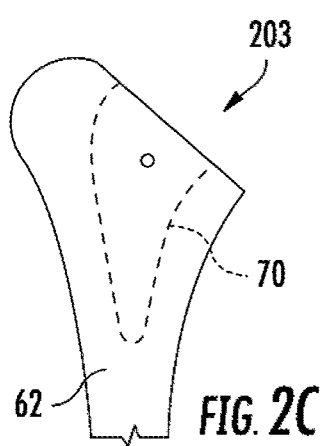
FIG. 2C is a schematic illustration of a step in a preoperative planning method for designing a shoulder surgery guide where the size of a humeral bone implant from Houndsfield units measured by computed tomography scan is determined, according to an embodiment of the disclosed subject matter.

In some embodiments, a pre-operative planning method for the humerus can comprise a step 203, as depicted in FIG. 2C, where the size of a humeral bone implant stem portion 70 can be determined from Houndsfield units (the Hounsfield scale, named after Sir Godfrey Newbold Hounsfield, is a quantitative scale for describing radiodensity) measured by CT scan. In some embodiments, this analysis can be accomplished virtually based on images taken from a subject or patient prior to surgery. By measuring the size of a humeral bone implant, data and information can be collected that informs the selection of a humeral head implant and/or supports the creation of a shoulder surgery guide device specific to the patient or subject to be treated.

Figure 2D:
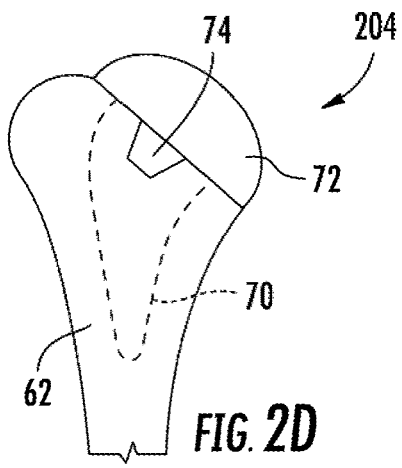
FIG. 2D is a schematic illustration of a step in a preoperative planning method for designing a shoulder surgery guide where a best fit size of implant from a range of sizes is determined, according to an embodiment of the disclosed subject matter.

In some embodiments, a pre-operative planning method for the humerus can comprise a step 204, as depicted in FIG. 2D, where a best fit size of humeral implant 72 (the humeral implant includes the humeral head 72 and the humeral stem 70) from a range of sizes can be determined. In some embodiments, the range of sizes can be selected from the group consisting of length of stem, size of humeral stem, diameter of stem, size diameter of head, height of head, and offset of the center spherical head compared to the center of the face of the humeral stem. In some embodiments, this analysis can be accomplished virtually based on images taken from a subject or patient prior to surgery. By determining the most appropriate size of humeral implant 72, data and information can be collected that informs the selection of a humeral head implant and/or supports the creation of a shoulder surgery guide device specific to the patient or subject to be treated.

Such planning steps particular to the humeral side of the joint can comprise analysis steps such as those depicted in FIGS. 2A-2D, and can comprise all or some of the steps depicted in FIGS. 2A-2D, and in some aspects can be done in any order desired. Alternatively, in some embodiments analysis steps particular to joint articulation can be performed first followed by analysis steps particular to fixation elements.

Figure 3:
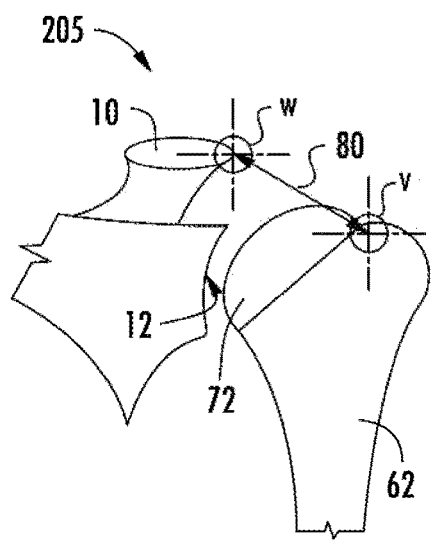
FIG. 3 is a schematic illustration of a step in a preoperative planning method for designing a shoulder surgery guide where vectors are compared in three dimensions to measure the distance of relocation of humeral tuberosity compared to the scapula, according to an embodiment of the disclosed subject matter.

In some embodiments, a pre-operative planning method for designing a shoulder surgery guide can comprise comparing vectors 80 in three dimensions to measure the distance of relocation of humeral tuberosity 72 compared to the scapula 10, as depicted in analysis 205 in FIG. 3. For example, there are 3 rotator cuff tendons that attach to the proximal humerus in the area of the greater tuberosity and the scapula. Such attachment points are depicted as v and w, respectively, in FIG. 3. These tendons control much of the rotation of the humerus about the scapula as well as having a part in elevating the humerus. If the vector resolved from these 3 tendons changes, kinematics and kinetics of the glenohumeral joint (joint comprising the glenoid and humerus) change. For example, changing the direction of vector 80 can change wear patterns and range of motion (ROM) of the implanted device versus the native joint. Additionally, in some embodiments, changing the magnitude of vector 80 by lengthening or increasing it with a joint prosthesis that is too large for the joint can result in decreased ROM, pain, and increased wear of the prosthetic components. Finally, changing the magnitude of vector 80 by decreasing or shortening it with a joint prosthesis that is too small for the joint can result in an unstable joint that may dislocate and can result in suboptimal mechanics for elevating the humerus. In some embodiments, this analysis can be accomplished virtually based on images taken from a subject or patient prior to surgery. By comparing vector 80 in three dimensions to measure the distance of relocation of humeral tuberosity 72 compared to the scapula 10, data and information can be collected that informs the selection of a humeral head implant, glenoid implant, and/or supports the creation of a shoulder surgery guide device specific to the patient or subject to be treated.

Figure 4:
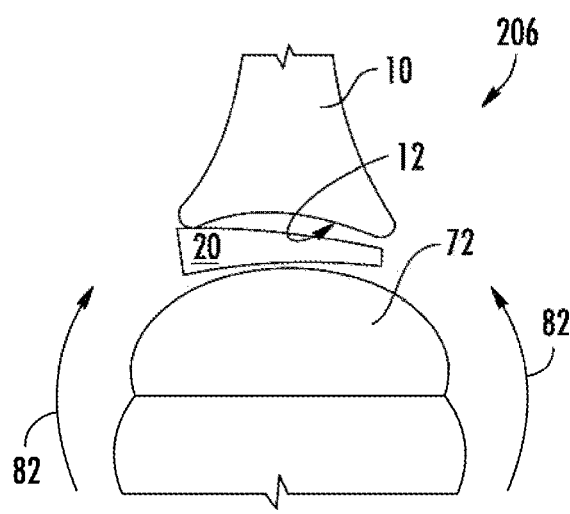
FIG. 4 is a schematic illustration of a step in a preoperative planning method for designing a shoulder surgery guide where range of motion analysis is conducted, including virtually positioning implants through extreme ranges of motion to measure impact locations and compensate for necessary functional range of motion, according to an embodiment of the disclosed subject matter.

In some embodiments, a pre-operative planning method designing a shoulder surgery guide can comprise a step 206, as depicted in FIG. 4, where range of motion (ROM) analysis 82 can be conducted, including virtually positioning implants 20, 72 through extreme ranges of motion to measure impact locations and compensate for necessary functional ROM. In some embodiments, this analysis can be accomplished virtually based on images taken from a subject or patient prior to surgery. By measuring the ROM with respect to glenoid implants 20 and/or humeral implants 72, data and information can be collected that informs the selection of glenoid implant, a humeral head implant and/or supports the creation of a shoulder surgery guide device specific to the patient or subject to be treated.

Figure 5:
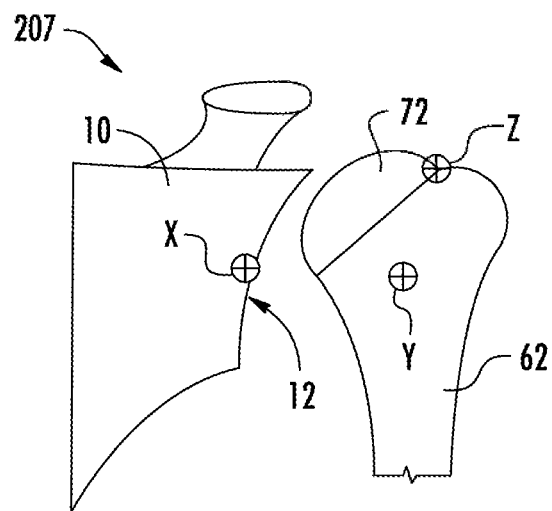
FIG. 5 is a schematic illustration of a step in a preoperative planning method for designing a shoulder surgery guide where soft tissue analysis comprising determining key soft tissue insertion points is conducted, according to an embodiment of the disclosed subject matter.

In some embodiments, a pre-operative planning method designing a shoulder surgery guide can comprise a step 207, as depicted in FIG. 5, where soft tissue, e.g. muscle, analysis is conducted. In some aspects, soft tissue analysis can comprise determining and/or assessing soft tissue insertion points (e.g., X, Y and Z) and analyzing impacts on and/or impacts from use of one or more implants (glenoid and/or humeral). In some embodiments, four rotator cuff muscles and their attachments points can be analyzed. For example, in some aspects analysis can comprise the subscapularis that attaches at an attachment point Y near the lesser tuberosity and at an attachment point X near the anterior glenoid. In some aspects analysis can comprise the supraspinatus that attaches at an attachment point Z near the anterior greater tuberosity and above the scapular spine (shoulder blade; not shown). In some aspects, soft tissue analysis can comprise the infraspinatus that attaches at the greater tuberosity (posterior to supraspinatus) and below the scapular spine (posterior). In some aspects, soft tissue analysis can comprise the teres minor that attaches posterior on the humerus and on the inferior scapular boder. In some embodiments, this analysis can be accomplished virtually based on images taken from a subject or patient prior to surgery. By analyzing the soft tissue around the glenohumeral joint, data and information can be collected that informs the selection of a glenoid implant, a humeral head implant and/or supports the creation of a shoulder surgery guide device specific to the patient or subject to be treated.

In some embodiments, the disclosed pre-operative planning methods can further comprise designing a shoulder surgery guide device, such as a glenoid placement device, based upon parameters collected from the planning methods and analyses. In some embodiments, a designed shoulder surgery guide can be produced, wherein the produced surgery guide can be configured in accordance with parameters collected from the planning and analysis specific to the patient to be treated. In some aspects, a guide, and/or a prosthetic implant, can be produced or made using a three dimensional (3D) printing device. In some embodiments, a shoulder surgery guide device produced as disclosed herein can comprise a polymeric or metallic material.

In some embodiments, the disclosed pre-operative planning methods can further comprise identifying a prosthetic shoulder implant, and/or identifying a placement position for the prosthetic shoulder implant. The identification of a prosthetic shoulder implant and placement position takes into consideration at least one of the factors selected from the group consisting of adjustments in glenoid implant size, augmentation depth, augment position, positioning in six degrees of freedom, fixation type, fixation size, reaming depth, reaming diameter, reaming angle, and/or a combination thereof. The above method can further comprise a step of recommending implants and placement positions, with recommended adjustments in humerus stem size, length, head diameter, head height, head offset and rotation (axial). A prosthetic shoulder implant can in some embodiments comprise a glenoid implant.

In some embodiments, the above methods of creating a shoulder surgery guide, including a glenoid placement guide, based on pre-operative planning can further comprise one or more optimization steps. Such optimization steps can comprise the identification of procedural risks based on measurements of one or more of a plurality of factors. Such factors can in some embodiments comprise whether the glenoid face coverage is maximized (e.g. about 0 to about 2 mm), the overhang of the glenoid face is minimized (e.g. about 0 to about 3 mm), and/or the bone removal on the glenoid face is minimized, such as for example less than about 2 mm of depth. Continuing, in some embodiments such optimization factors can comprise whether the glenoid retroversion is less than about 5 degrees to about 10 degrees, the seating of the glenoid implant is greater than about 80%, i.e. about 80% of the back side of the glenoid implant is supported by or touching bone, whether there is minimized penetration of the glenoid cortical wall anteriorly (e.g. about 0 mm to about 3 mm), and/or the depth of any glenoid implant augment feature is as minimal as possible. Still yet, in some embodiments such optimization factors can comprise whether there is less than about 1 mm of difference between the anatomic joint line and the new joint line with implants, there is minimized penetration of the glenoid cortical wall anteriorly, and/or there is maximized bone thickness behind the glenoid, preferably greater than 3 mm. In some embodiments such optimization factors can comprise whether the orientation offset between the native glenoid and implant superior/inferior axis is minimized, preferably less than 5 degrees, the superior or inferior tilt versus native glenoid is minimized, preferably less than 5 degrees, there is less than about 5% to about 10% change in soft tissue length at extreme ranges of motion, there is maximized filing of the humeral metaphysis, in some embodiments greater than about 90% of metaphyseal bone filled based on and identification of metaphyseal bone by use of Houndsfield units, there is an absence of a humeral head overhang compared to the cut, or prepared surface of the humeral bone, there is minimal difference in humeral head diameter between anatomic and implant, in some embodiments less than about 3 mm, there is minimal difference in humeral head height between anatomic and implant, in some embodiments less than about 1 mm, and/or there is greater tuberosity to medial head edge comparison to anatomic, in some embodiments less than about 2 mm. In some embodiments, such procedural risks (any and/or all from the above list) can be determined virtually based on images taken from a subject prior to surgery.

Figure 6:
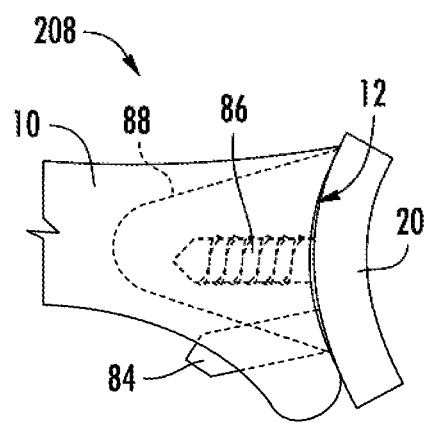
FIG. 6 is a schematic illustration of a step in a preoperative planning method for designing a shoulder surgery guide where penetration of the cortical wall anteriorly of the vault is assessed, according to an embodiment of the disclosed subject matter.

With respect to the above optimization steps that comprise the identification of procedural risks, in some embodiments the penetration of the cortical wall anteriorly of the vault can be assessed, as depicted in FIG. 6. FIG. 6 depicts step 208 of assessing the penetration of the cortical wall anteriorly of the vault 88 by a support structure 84 of glenoid implant 20. In some embodiments, an additional or alternate support structure 86 can be used to affix implant 20 to glenoid 12.

Figure 7:
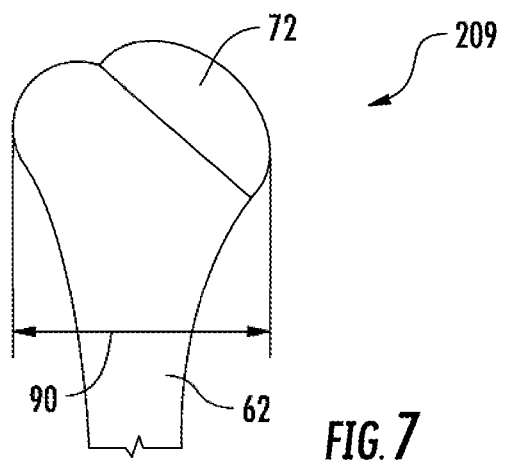
FIG. 7 is a schematic illustration of a step in a preoperative planning method for designing a shoulder surgery guide where the width of the greater tuberosity to medial head edge with an implant is compared to the anatomic width, according to an embodiment of the disclosed subject matter.

Also with respect to the above optimization steps that comprise the identification of procedural risks, in some embodiments the width of the greater tuberosity to medial head edge with an implant can be compared to the anatomic width. For example, in FIG. 7 the width 90 of the greater tuberosity to medial head edge with an implant 72 can be compared to the width of the anatomical humeral head.

In some aspects, the planning methods and analysis steps disclosed herein can be done pre-operatively. That is, they can be done prior to surgery in a virtual or software-based environment. Such virtual simulations can in some embodiments be based on images or scans taken from a subject prior to surgery. Currently available and future imaging techniques, e.g. computed tomography (CT), x-ray imaging, positron emission tomography (PET), ultrasound, etc., can be used to capture images and data to be used in simulation-based analysis and planning to identify suitable prosthetic implants and/or design surgery guides. By using images captured from a subject or patient to be treated, the analysis and results can be specific to the subject or patient and can take into consideration the particularities of that subject's condition.

In some aspects, when the pre-operative planning is conducted, particularly with respect to designing and producing a glenoid placement guide as disclosed herein, the actual morphologic form of the native glenoid bone of a patient to be treated is considered and imaged. In order for the positioning of the glenoid placement guide to be correct, the form of the glenoid as found on a CT scan, for example, is used to create a "reverse image" that is incorporated in the guide design.

The subject matter described herein may be implemented in software in combination with hardware and/or firmware. For example, the subject matter described herein may be implemented in software executed by a processor. In one exemplary implementation, the subject matter described herein may be implemented using a computer readable medium having stored thereon computer executable instructions that when executed by the processor of a computer control the computer to perform steps. Exemplary computer readable media suitable for implementing the subject matter described herein include non-transitory devices, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

As such, in some embodiments the disclosed pre-operative planning methods can further comprise providing a computer readable medium having stored thereon executable instructions that when executed by the processor of a computer control the computer to perform one or more of the planning method and/or analysis steps. For example, in some embodiments computer readable medium can have stored thereon executable instructions that when executed by the processor of a computer can control the computer to generate a virtual 3D model of a glenoid guide device, e.g. a glenoid placement guide, reflecting one or more optimized parameters determined during pre-operative planning. Additionally, in some aspects, computer readable medium can have stored thereon executable instructions that when executed by the processor of a computer control the computer to control a 3D printing device in communication with the computer, whereby the 3D printing device can print a glenoid guide device or humeral guide device for use in shoulder replacement surgery in a patient for which pre-operative planning method steps were conducted.

Further, in some aspects of the disclosed methods, systems and devices, a computer readable medium can be provided having stored thereon executable instructions that when executed by a processor of a computer can control the computer to generate a virtual 3D model of a glenoid implant device or placement guide device reflecting one or more optimized parameters determined during pre-operative planning. Thus, in some embodiments a computer readable medium is provided, wherein the computer readable medium has stored thereon executable instructions that when executed by the processor of a computer control the computer to perform one or more of the planning method and/or analysis steps as disclosed herein.

It should be noted that the computers, computing devices, hardware and/or functionality described herein may constitute a special purpose test device. Further, computers, computing devices, hardware and/or functionality described herein can improve the technological field of pre-operative planning for shoulder surgery and can improve generation of virtual modeling systems.

The subject matter described herein for generating 3D models of glenoid and/or humeral implant devices, and/or for modeling and virtually simulating pre-operative shoulder surgery analysis improves the likelihood of a positive outcome from shoulder surgery. It should also be noted that a computing platform, computer, computing device, and/or hardware that implements the subject matter described herein may comprise a special purpose computing device usable to generate 3D models of glenoid and/or humeral implant devices, and/or for modeling and virtually simulating pre-operative shoulder surgery analysis.

As used herein, the term "node" refers to a physical computing platform including one or more processors and memory.

As used herein, the terms "function" or "module" refer to hardware, firmware, or software in combination with hardware and/or firmware for implementing features described herein.

In some embodiments a computer readable medium is provided, having stored thereon executable instructions that when executed by the processor of a computer control the computer to perform steps comprising generating a virtual three dimensional model of a glenoid and/or humeral guide reflecting one or more optimized parameters determined during pre-operative planning based on the above method steps. In some embodiments, a computer readable medium is provided, having stored thereon executable instructions that when executed by the processor of a computer control a 3D printing device in communication with the computer, whereby the 3D printing device prints a glenoid and/or humeral guide, or placement guide, for use in shoulder replacement surgery in a patient for which the optimization analysis was conducted.

Figure 8A:
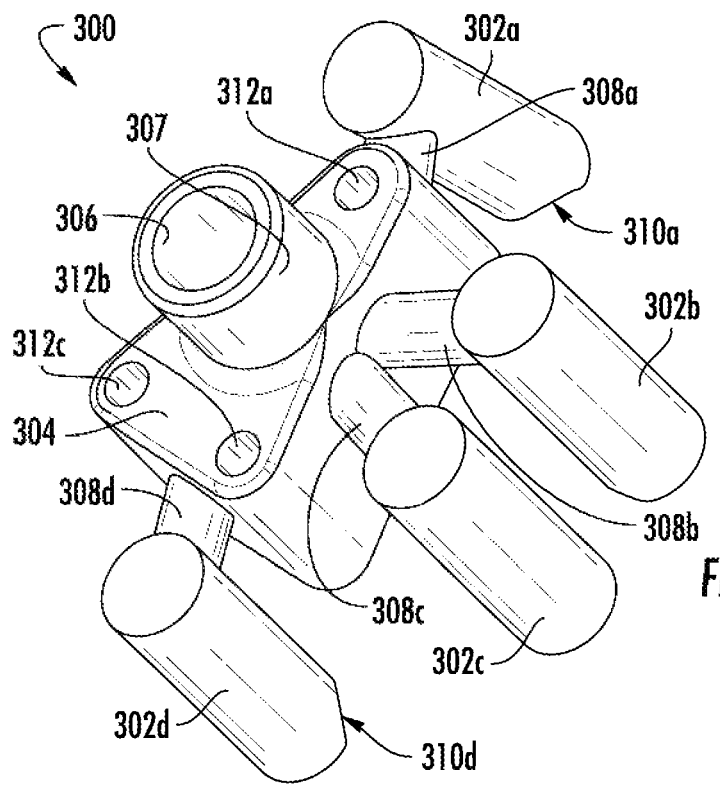
FIGS. 8A and 8B are perspective front and rear views, respectively, of a glenoid guide, according to an embodiment of the disclosed subject matter.
Figure 8B:
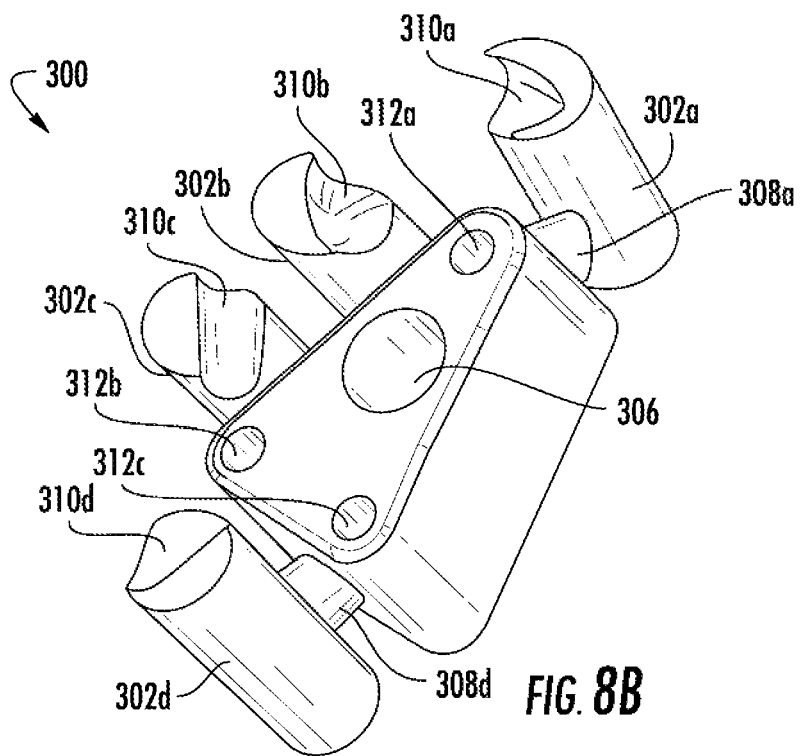

Based on the pre-operative planning steps and analyses disclosed herein, in some embodiments shoulder surgery guides or guide devices, and particularly glenoid placement guide devices, can be designed, simulated and in some instances produced for use in shoulder replacement surgery. Such a surgery guide device is depicted in FIGS. 8-13. FIGS. 8A and 8B are perspective front and rear views, respectively, of a glenoid guide, according to an embodiment of the disclosed subject matter. As depicted in FIGS. 8A and 8B, glenoid placement guide 300 can in some embodiments comprise a plurality of peripheral guide structures 302 configured to align with the edge or rim of the glenoid face and/or glenoid surface. In FIGS. 8A and 8B four peripheral guide structures 302, namely 302*a*, 302*b*, 302*c*, and 302*d*, are shown, but any number of peripheral guide structures 302, including for example 2, 3, 4, 5, 6, 7, 8, 9 or 10, could be used so long as there are a sufficient number to align and stabilize glenoid placement guide 300 on a glenoid face (see FIGS. 9, 10 and 12 for a depiction of the guide in use). In some embodiments, peripheral guide structures 302*a*, 302*b*, 302*c*, and 302*d* can each comprise a corresponding indentation or cupped surface 310*a*, 310*b*, 310*c*, and 310*d*, most clearly visible in FIG. 8B, that can be configured to wrap over the edge of, or matingly align with, the rim of the glenoid (see glenoid 12 and glenoid rim 13 in FIG. 9 for example). Cupped surface 310*a*, 310*b*, 310*c*, and/or 310*d* can secure and/or stabilize guide 300 at the desired and predetermined (based on the pre-operative analysis and guide design) location on the glenoid. In some embodiments, some peripheral guide structures may not include a cupped surface, or may include a different shaped structure, as needed to accommodate and align with a given point along the edge of a glenoid in a subject to be treated. Each peripheral guide structure 302, and corresponding cupped surface 310, can be predetermined and configured based on individual datum points collected during a pre-operative analysis and guide design, as disclosed herein, such that glenoid placement guide 300 is patient-specific, i.e. custom designed to fit the shape, size, curvature and natural condition of the glenoid of a patient to be treated.

Peripheral guide structures 302a, 302b, 302c, and 302d generally extend radially from a hub structure 304, and can be positioned and secured to hub structure 304 by radial arms 308a, 308b, 308c, and 308d. Of course, the number of radial arms 308 will be dictated by, and correspond to, the number of peripheral guide structures 302. The length of radial arms 308 can be determined and configured based on individual datum points collected during a pre-operative analysis and guide design, as disclosed herein, such that each of the peripheral guide structures 302 align with the rim of the glenoid at the desired location.

Hub structure 304 as depicted in FIGS. 8A and 8B comprises a triangular structure, but can be any desired shape, e.g. square, rectangular, circular or octagonal. Hub structure 304 can comprise a central port 306 comprising a cylindrical opening extending through the entire length of hub structure 304 and providing an opening through which a pin, depth-control pin, drill or boring device can be guided to create an opening, i.e. drill a hole, and/or place a guide pin in the glenoid face. As depicted in FIGS. 8A and 8B, central port 306 can in some embodiments comprise an extend portion that extends beyond the upper surface of hub structure 304 by virtue of cylindrical housing 307. Cylindrical housing 307, along with central port 306, can provide an opening through which a pin, depth-control pin, drill or boring device can be guided to the surface of the glenoid, and particularly a predetermined point or location on the glenoid surface, with cylindrical housing 307 providing a stabilizing force and support for guiding the pin, depth-control pin, drill or boring device. Cylindrical housing 307 can also act as a depth guide wherein it can be used as an indicator for the depth of a depth-control pin 400 (see FIG. 1I discussed below). That is, a collar 420 of depth-control pin 400 can stop or match up with a top rim portion of cylindrical housing 307 to set the depth of depth-control pin 400.

With peripheral guide structures 302a, 302b, 302c, and 302d aligning with the rim or edge of the glenoid, hub structure 304, by virtue of its attachment to each of peripheral guide structures 302a, 302b, 302c, and 302d, can be aligned at the predetermined and desired location on the face of a glenoid. The location of hub structure 304, and particularly central port 306, can be predetermined and configured based on pre-operative analysis such that central port 306, and in some embodiments cylindrical housing 307, provides a steady and secure guide to the location on the glenoid where a prosthesis or implant is to be attached.

Continuing with FIGS. 8A and 8B, in some embodiments, hub structure 304 of glenoid placement guide 300 can further comprise one or more anchor pin ports 312. As depicted in FIGS. 8A and 8B, hub structure 304 can comprise three anchor ports, shown as anchor ports 312a, 312b and 312c. However, a glenoid placement guide 300 as disclosed herein can comprise any number of anchor pin ports 312, including for example 0, 1, 2, 3, 4, 5, 6, 7, 8, 9 or 10, so long as there are a sufficient number to anchor and/or temporarily secure glenoid placement guide 300 to a glenoid face, if necessary, while a hole is drilled through central port 306 and/or a depth-control pin is inserted. Indeed, in some embodiments a glenoid placement guide 300 is provided with no (zero) anchor pin ports 312 since in some embodiments a glenoid placement guide 300 can be used without having to use anchor pins.

Figure 9:
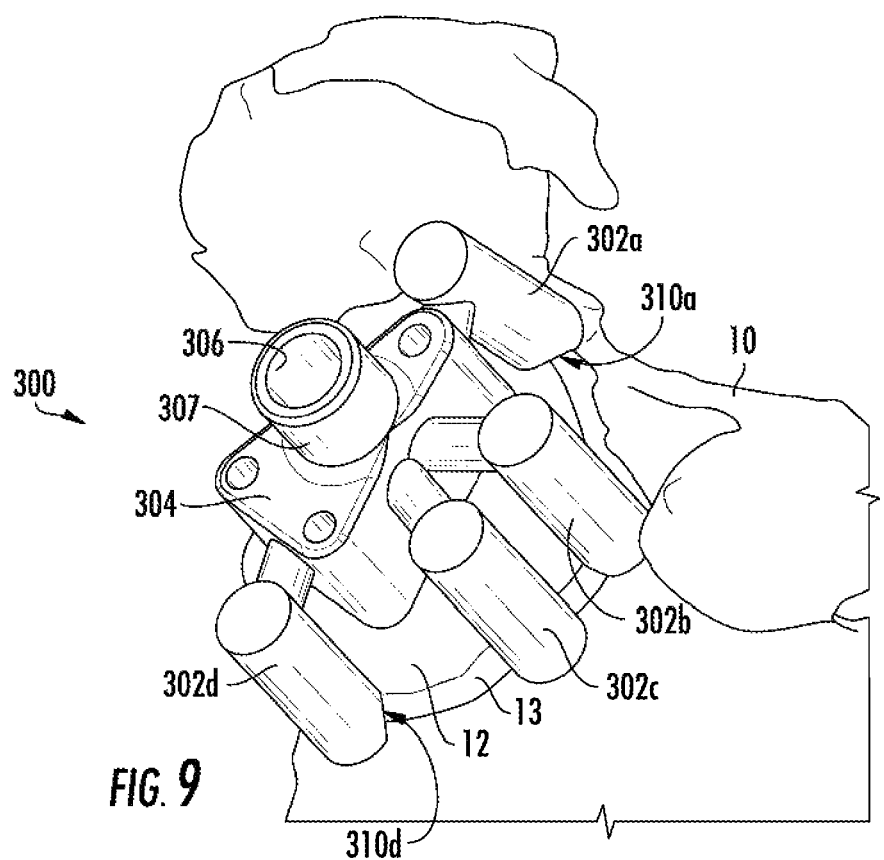
FIG. 9 is a perspective view of a glenoid guide fitted to a glenoid on a scapula bone, according to an embodiment of the disclosed subject matter.

FIG. 9 depicts glenoid placement guide 300 in use, or aligned with the face of glenoid 12 on scapula 10. Cupped surfaces 310a, 310b, 310c, and 310d wrap over the edge of the rim 13 of the glenoid 12 such that guide 300 is aligned with and stabilized over glenoid 12. With guide 300 in place on glenoid 12, a pin, depth-control pin, drill or boing device can be inserted into central port 306, which can guide the pin, depth-control pin, drill or boing device to the precise location on glenoid 12 where a predetermined attachment point, or reaming depth-control insertion point, is located based on pre-operative analytics.

Figure 10:
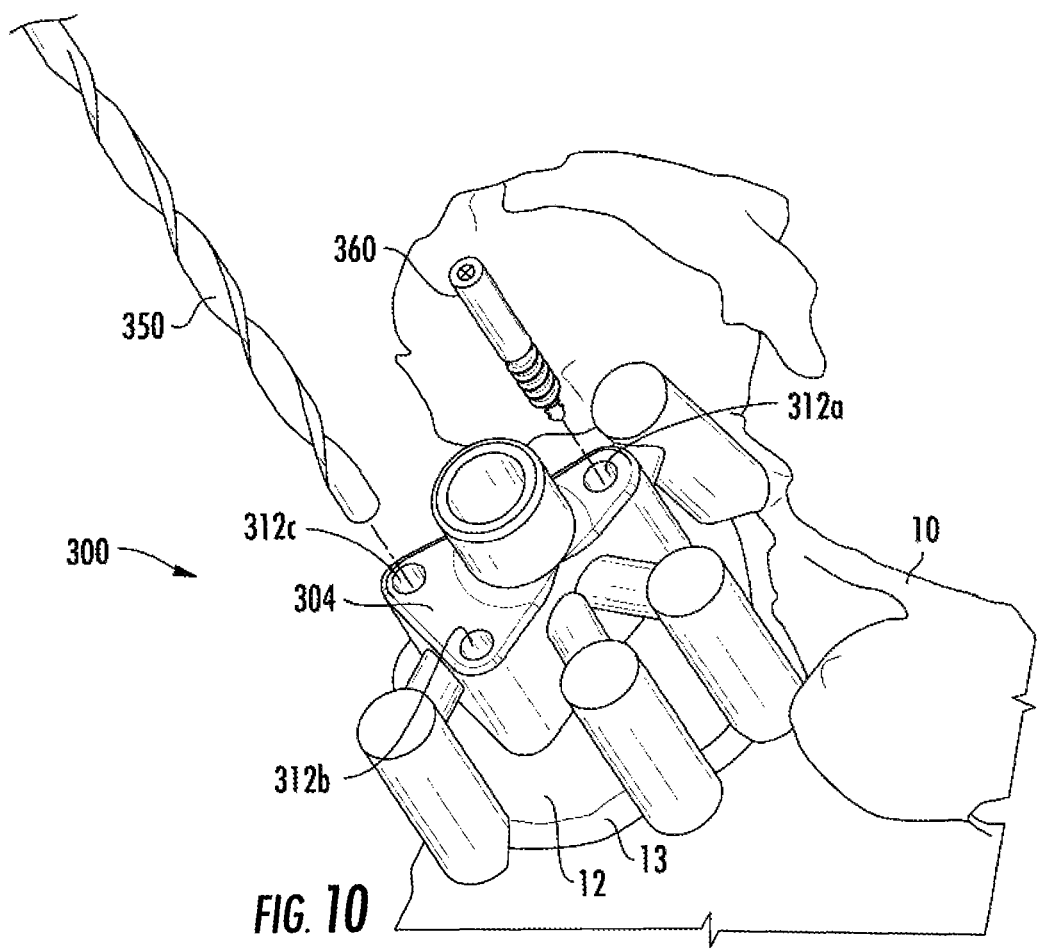
FIG. 10 is a perspective view of a glenoid guide fitted to a glenoid on a scapula bone with a drill, according to an embodiment of the disclosed subject matter.
Figure 11:
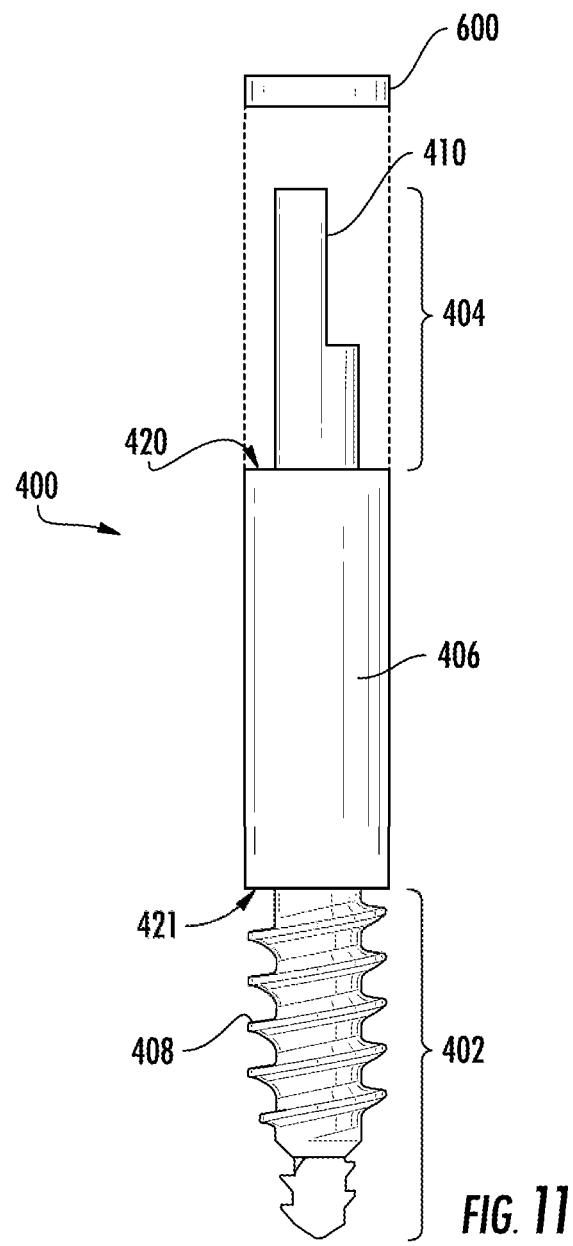
FIG. 11 is a side view of a depth-control pin, according to an embodiment of the disclosed subject matter.

FIG. 10 illustrates glenoid placement guide 300 in use, or aligned with the face of glenoid 12 on scapula 10, with the use of drilling bit 350 and/or anchor pin 360. When it is desirable and/or necessary to anchor, even temporarily, glenoid placement guide 300 to glenoid 12, an anchor pin 360, or in some aspects multiple anchor pins, can be inserted into one or more anchor pin ports 312 and screwed into glenoid 12. In some aspects, drilling bit 350 can be used to create a hole or holes in the glenoid surface prior to insertion of an anchor pin 360.

A depth-control pin 400, also referred to as a reaming depth-control pin, is illustrated in FIG. 1I. Depth-control pin 400 can be used to control the depth, orientation and angle of reaming of a glenoid surface or glenoid face. As illustrated in FIG. 1I, depth-control pin 400 can comprise a cylindrical shaft 406 having a first end 402 and a second end 404. First end 402 can comprise a threaded portion 408 configured to threadingly engage an opening in a glenoid bone (possibly created by a drill bit 350 or similar boring device), and/or configured to threadingly screw into the surface of a glenoid bone, i.e. self tapping. Depth-control pin 400 can in some embodiments screw into or penetrate a glenoid bone up to a depth equal to the length of first end 402 and/or the length of threaded portion 408. In some embodiments, depth-control pin 400 can in some embodiments screw into or penetrate a glenoid bone up until collar 421 comes into contact with the glenoid surface, or where the threads end. That is, collar 421 acts as a depth stop once it reaches the surface of the glenoid. The depth can be generated by the Glenosys depth-control pin 400. Once depth-control pin 400 is secured to the glenoid via the threaded portion 408, reaming depth is controlled by the length of section 406 which controls the location of collar 420 in conjunction with the internal mating geometry of a reamer (see, e.g., FIG. 13B). Length of cylindrical portion 406 and consequently location of collar 420 can be determined via the preoperative analysis performed by software as disclosed herein. The reaming depth can be the result of the software analysis to determine the amount of backside support desired by a user, e.g. a surgeon. Typically greater than about 80% backside support for a given implant is desired. More reaming or more depth of reaming can in some aspects result in a shorter length of section 406, resulting in collar 420 being closer to the glenoid face. Less reaming depth can result in a longer length of section 406 placing the location of collar 420 farther from the glenoid face.

Figure 13A:
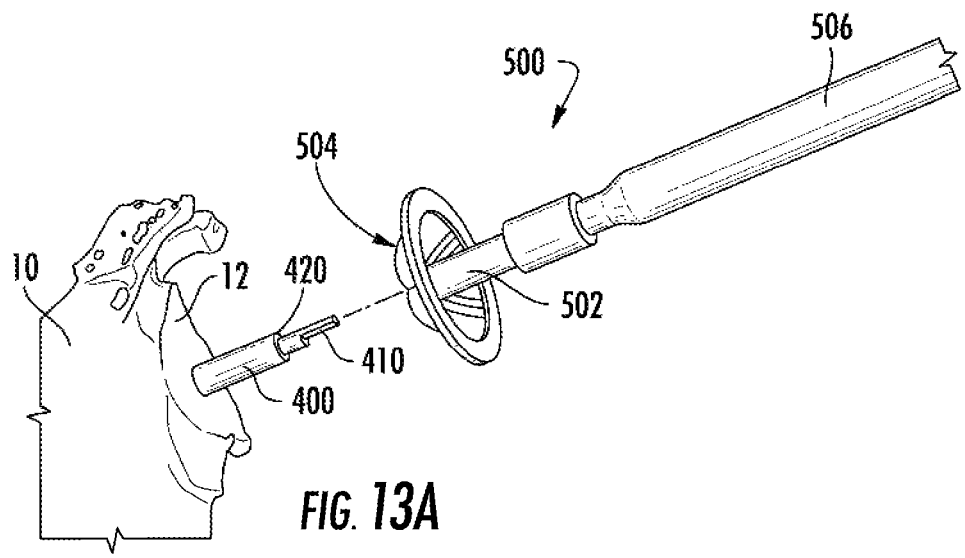
FIGS. 13A and 13B are perspective views of a depth-control pin affixed to a glenoid on a scapula bone prior to receiving (FIG. 13A) and after receiving (FIG. 13B) a reamer device, according to an embodiment of the disclosed subject matter.
Figure 13B:
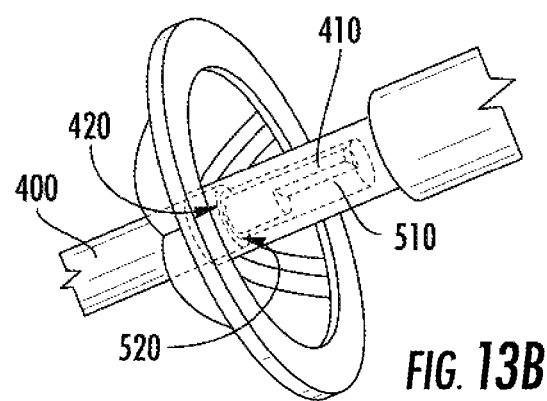

Second end 404 of depth-control pin 400 can comprise a cylindrical shaft configured to receive a glenoid reaming device (see FIGS. 13A and 13B). The cylindrical shaft of second end 404 can engage an internal diameter and mating geometry of a reamer.

Indented portion 412 can in some embodiments act as a quick connect mechanism. Of note, indented portion 412 is only exemplary of a connection mechanism and is optional for depth-control pin 400. Likewise, in some embodiments, notched portion 410 can be configured to engage a tool (e.g. guide sleeve 700 in FIG. 12B) or drill to apply a rotational and/or downward force to cause depth-control pin 400 to engage, i.e. screw into, the surface of a glenoid bone. In some aspects, notched portion 410, instead of being a notch, or in addition to the notch, can comprise a hex head, slot, port or torx head configured to engage or receive a tool capable of applying rotational and/or downward force to depth-control pin 400. Other connection mechanisms for depth-control pin 400, and particularly second end 404, can be used without departing from the scope of the instant disclosure.

In some embodiments, collar 420 can be located between threaded first end 402 and receiving second end 404. For example, collar 420 (also referred to as a shoulder in some aspects, but distinct from shoulder 421) can be at the top of cylindrical shaft 406 and near the base of second end 404. Collar 420 can act as a stop for a reaming device inserted over receiving portion 410. That is, collar 420 can control the depth of reaming by a reaming device when depth-control pin 400 is screwed or otherwise affixed to a glenoid surface.

Figure 12A:
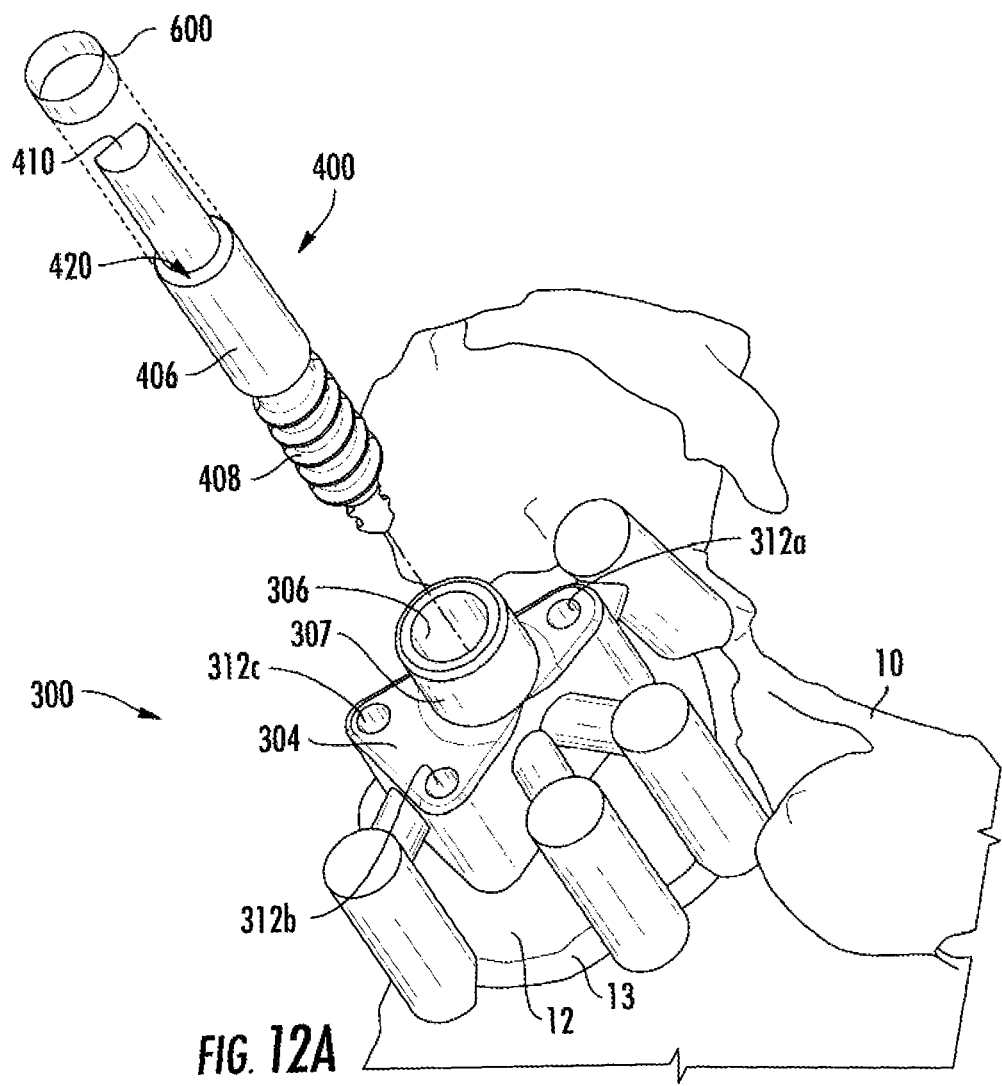
FIGS. 12A and 12B are perspective views of a glenoid guide fitted to a glenoid on a scapula bone prior to (FIG. 12A) and after (FIG. 12B) a depth-control pin is inserted, according to an embodiment of the disclosed subject matter.
Figure 12B:
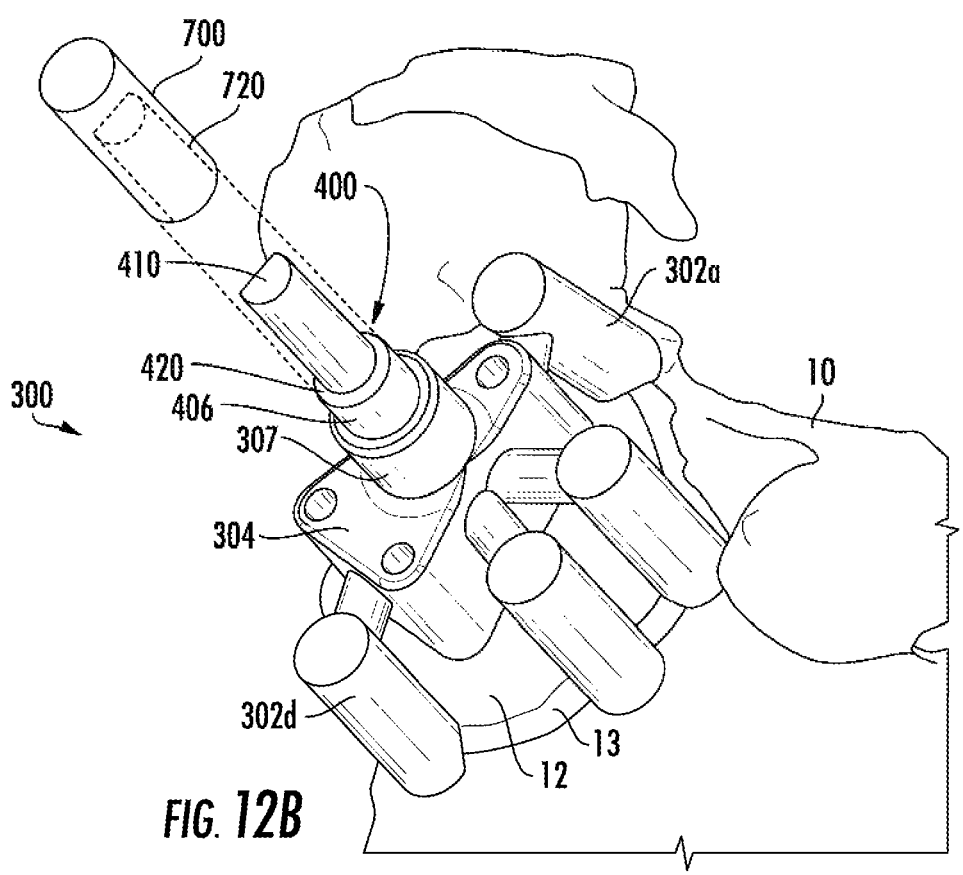

FIGS. 12A and 12B illustrate glenoid placement guide 300 in use, or aligned with the face of glenoid 12 on scapula 10, with the use of depth-control pin 400. FIG. 12A shows depth-control pin 400 prior to insertion in central port 306, while FIG. 12B shows depth-control pin 400 after insertion into central port 306 and/or during the threading of depth-control pin 400 into glenoid surface 12. Note that cylindrical shaft 406 is configured to slidingly engage the cylindrical opening of the central port 306. In some aspects, cylindrical shaft 406 has a diameter substantially similar to but slightly less than the diameter of central port 306.

In some embodiments, depth-control pin 400 can be guided through central port 306 of glenoid placement guide 300 and forced into glenoid bone 12 using a tool or guide sleeve 700 as depicted in FIG. 12B. Guide sleeve 700 can be patient specific and designed along with glenoid placement guide 300 and/or depth-control pin 400 during pre-operative planning as disclosed herein. In some embodiments, an alignment surface of glenoid placement guide 300, e.g. an upper end of cylindrical housing 307, can act as a depth guide wherein it can be used as an indicator for the depth of a depth-control pin 400, to thereby achieve the appropriate reaming depth, such as to achieve about 80% implant support. That is, collar 420 of depth-control pin 400 can stop or match up with a top rim portion of cylindrical housing 307 to set the depth of depth-control pin 400. Guide sleeve 700 can in some aspects be used to engage second end 404 of depth-control pin 400, such as by engaging notch 410 or other mechanical linkage, to thereby force, through tapping, pushing and/or turning, depth-control pin 400 into placement guide 300 such that collar 420 is aligned with cylindrical housing 307. In some embodiments, once these two surfaces are flush, depth-control pin 400 can be in its correct depth to control the preplanned reaming depth.

After depth-control pin 400 is threaded into the surface or face of glenoid 12 at the desired location on glenoid 12, as controlled by glenoid placement guide 300, glenoid placement guide 300 can be removed by pulling it away from, i.e. sliding it off of, depth-control pin 400 such that depth-control pin 400 remains embedded or screwed in glenoid 12. See FIG. 13A. Glenoid 12 as depicted in FIG. 13A is now ready to be reamed using reaming device 500 guided by depth-control pin 400. However, before reaming the stability of depth-control pin 400 can be assessed.

It is possible that depth-control pin 400 can be seated at a pre-planned depth, as discussed above, and yet it is unstable (or at least not stable enough to support reaming) once placement guide 300 is removed. In order to stabilize depth-control pin 400 it can in some embodiments need to be screwed deeper into glenoid 12. However, doing so alters the depth control aspect of depth-control pin 400 for subsequent reaming. Thus, the location or height of shoulder 420 must be adjusted or augmented to achieve the same desired depth control after depth-control pin 400 is further seated to achieve the necessary stability. In such an embodiment a depth control augment 600, i.e. a spacer, can be used. See FIGS. 11 and 12A.

Depth control augment 600 can in some aspects be a washer, ring, sleeve or cylindrical structure having a substantially similar, or the same, outside diameter as cylindrical portion 406 of depth-control pin 400, and an inside diameter sufficient to allow it to slide over second end 404 of depth-control pin 400. When in use depth control augment 600 can effectively increase the height of, or raise the location of, shoulder 420. In some aspects, depth control augment 600 can have a height of about 1 mm, about 2 mm, about 3 mm, about 4 mm, about 5 mm, about 6 mm, about 7 mm, about 8 mm, about 9 mm, or about 10 mm. When slid over second end 404 of depth-control pin 400 it can be advanced by guide sleeve 700. One or more depth control augments 600 can be used such that the number of millimeters depth-control pin 400 is advanced into glenoid 12 beyond that which was originally intended can be compensated by the addition the one or more depth control augments 600. For example, if depth-control pin 400 is advanced into glenoid 12 4 mm more than originally intended in order to achieve sufficient stability one 4 mm depth control augment 600, or two 2 mm depth control augments 600, can be used to achieve the same depth control for which depth-control pin 400 was designed.

Glenoid 12 as depicted in FIG. 13A is now ready to be reamed using reaming device 500, while being guided by depth-control pin 400. Reaming device 500 can comprise a shaft 506, reaming head 504, and connector 502 connection reaming head 504 to shaft 506. Inside head 504 can be a cavity 510 with shoulder 520.

Reaming device 500 can slidingly engage second end 404, i.e. the receiving portion, of depth-control pin 400 by receiving second end 404 into cavity 510 of reaming device 500. See FIG. 13B. Collar 420 can abut shoulder 520 in cavity 510 such that reaming device 500 can only slidingly engage depth-control pin 400 up to a predetermined depth. That is, collar 420 acts as a depth-control device on depth-control pin 400 to limit the distance reaming device 500 can travel down depth-control pin 400, and by virtue the depth of the reaming of glenoid 12 caused by reaming face 504.

Thus, in some embodiments a glenoid placement guide is provided, comprising a hub, one or more radial arms extending substantially perpendicularly and radially from the hub, one or more peripheral guide structures affixed to the one or more radial arms, and a central port comprising a cylindrical opening passing through the hub. Such a glenoid placement guide can further comprise one or more anchoring pin channels, wherein each channel can comprise a cylindrical opening passing through the hub and configured to receive and guide an anchoring pin to an anchoring location of a glenoid surface. The central port can comprise a cylindrical opening passing through the hub and configured to receive and guide a depth-control pin to a predetermined location on a glenoid surface. The glenoid placement guide can in some aspects comprise a polymeric or metallic material.

In some aspects, one or more peripheral guide structures are matched to the surface or rim of a glenoid of a patient to be treated. Such peripheral guide structures that are matched to the surface of a glenoid of a patient to be treated are configured to align the glenoid placement guide on the glenoid. To do this, in some embodiments the terminal end of each peripheral guide structure can comprise a cupped surface configured to align with an edge portion or rim of the glenoid surface of the patient to be treated. The orientation and alignment of the peripheral guide structures to match the surface or rim of a glenoid of a patient to be treated is achieved through pre-operative planning. By doing so the peripheral guide structures orient the placement guide on the glenoid such that the central port is positioned at a predetermined or optimal position on the glenoid for placement of a reaming depth-control pin. Not only is the location of the depth-control reaming pin controlled by the design of the glenoid placement guide, but the angle, direction, orientation and depth of the depth-control pin is dictated by the glenoid placement guide such that once the depth-control pin is affixed to the glenoid it guides the reaming device to achieve the desired reamed glenoid surface. The depth, angle, orientation and location of the reaming is all controlled by the precise and predetermined placement of the depth-control pin, which is dictated by the glenoid placement guide, which is designed based on pre-operative planning.

The pre-operative planning to match the glenoid guide structure to the surface or rim of the glenoid can in some embodiments comprise aligning an anterior edge of a glenoid implant with an anterior edge of a glenoid bone; adjusting a retroversion of the glenoid implant; adjusting an augmentation of the glenoid implant; adjusting an inferior tilt of the glenoid implant; evaluating bone support for the glenoid implant, wherein an amount of a rear surface of the glenoid implant that is supported by or touching bone is assessed; adjusting a medialization of the glenoid implant by assessing the volumetric amount of bone needed to be removed by reaming, or the minimum total distance of reaming necessary, in order to optimize the bone to implant interface; analyzing fixation support in the absence of central pegs that penetrate a vault medially; analyzing a joint line, comprising comparing an original joint line and a new joint line, wherein the new joint line is substantially similar to the original joint line; measuring and matching widths of the glenoid implant and the glenoid bone after reaming and aligning inferior and superior axes of the glenoid implant and bone; assessing and adjusting as needed a thickness/height of the glenoid implant; assessing and adjusting as needed a depth of a glenoid fossa; and assessing and adjusting as needed a thickness of a graft.

Such pre-operative planning to match the guide structures to the surface of the glenoid can be done virtually based on images taken from the subject prior to surgery, as discussed further herein. The glenoid placement guide can then be designing, configured and produced based upon parameters collected from the pre-operative planning such that the guide can act to orient a depth-control pin such that it an guide the depth, orientation, direction, angle and location of a reaming device.

The pre-operative planning that goes into designing the glenoid placement guide can in some embodiments further comprise taking into consideration the humeral side of the joint and its impacts on the glenoid. For example, the pre-operative planning to match and orient the peripheral guide structures to the surface of the glenoid can further comprise: determining a diameter of a humeral head; determining a height of the humeral head; determining a size of humeral bone implant from Houndsfield units measured by computed tomography scan; and determining a best fit size of humeral implant from a range of sizes, wherein the range of sizes is selected from the group consisting of length of stem, size of humeral stem, diameter of stem, size diameter of head, height of head, and offset of the center spherical head compared to the center of the face of the humeral stem. Moreover, in some aspects, the pre-operative planning to match the guide structures to the surface of the glenoid can further comprise identifying a prosthetic shoulder implant, and identifying a placement position for the prosthetic shoulder implant, wherein the identification of the prosthetic shoulder implant and placement position can take into consideration at least one of the factors selected from the group consisting of adjustments in humerus stem size, length, head diameter, head height, head offset and rotation (axial), and/or combinations thereof.

Still yet, in some aspects, the pre-operative planning can comprise: comparing vectors in three dimensions, wherein the vectors comprise a distance and direction between tendon and muscle insertions on a scapula and a humerus of a subject, wherein the vectors measure the distance of relocation of humeral tuberosity compared to the scapula; determining a suitable implant based on comparison of the vectors; and designing a glenoid placement guide based on the comparison of vectors and determination of implant.

Still yet, in some aspects, the pre-operative planning can comprise: conducting range of motion analysis, including virtually positioning implants through extreme ranges of motion to measure impact locations and compensate for necessary functional range of motion; determining a suitable implant based on comparison of the vectors; and designing a glenoid placement guide based on the range of motion analysis and determination of implant. And in some embodiments the pre-operative planning can comprise: conducting soft tissue analysis comprising determining key soft tissue insertion points; measuring distances in three dimensions for comparison to pre-operative conditions; assessing lengths at extreme ranges of motion, such that total soft tissue length change or contraction is substantially maintained within anatomical ranges in order to substantially achieve most common activities of daily living; determining a suitable implant based on comparison of the vectors; and designing a glenoid placement guide based on the range of motion analysis and determination of implant. The pre-operative planning can also comprise in some aspects identifying procedural risks by determining: whether a glenoid face coverage is maximized; whether an overhang of the glenoid face is minimized; whether bone removal on the glenoid face is minimized; whether the glenoid retroversion is less than about 5 to about 10 degrees; whether seating of the glenoid implant is greater than about 80% of the implant coverage area; whether there is minimized penetration of the glenoid cortical wall anteriorly;

whether there is greater than about 3 mm bone thickness behind glenoid; whether the orientation offset between the native glenoid and implant superior/inferior axis is less than about 5 degrees; whether the superior or inferior tilt versus native glenoid is less than 5 degrees; whether there is an absence of a humeral head overhang compared to the cut, or prepared surface of the humeral bone; whether there is less than about 3 mm difference in humeral head diameter between anatomic and implant; whether there is less than about 1 mm difference in humeral head height between anatomic and implant; and whether there is less than about 2 mm greater tuberosity to medial head edge in comparison to anatomic; whereby procedural risks are identified; and designing a glenoid placement guide based on the identified procedural risks.

In some embodiments, a kit is provided for pre-operatively planned shoulder surgery, including glenoid reaming. Such a glenoid placement guide kit can in some embodiments comprise a glenoid placement guide of claim 1; a depth-control pin; and a reaming device. In some aspects, the kit can further comprise one or more anchoring pins. In some aspects, the kit can further comprise a software program or computer readable medium for conducting the pre-operative analysis and analyzing images of shoulder joint to be treated. In some aspects, instructions for conducting the analysis, creating a glenoid placement guide and/or using the guide are also provided in the kit.

In some embodiments, methods of reaming a glenoid bone surface of a patient in preparation for glenoid surgery are provided. Such methods can comprise designing and producing a patient-specific glenoid placement guide, wherein the guide comprises a central port configured to receive a depth-control pin and guide it to a predetermined location on the glenoid surface and/or designing and producing, or providing, a depth-control pin. The methods can further comprise placing a placement guide on a glenoid surface of the patient, inserting a depth-control pin through the guide central port, turning the depth-control pin whereby the pin engages the glenoid surface, removing the guide from the glenoid surface, whereby the depth-control pin remains engaged to the glenoid surface, aligning a reaming device to the glenoid surface by sliding the reaming device over the depth-control pin, and reaming the surface of the glenoid, whereby the depth and orientation of the reaming is controlled by the depth-control pin. In some embodiments, a guide sleeve can be used to adjust and confirm positioning of the depth-control pin.

In some embodiments, methods of reaming a glenoid bone surface, including designing and producing a patient-specific glenoid placement guide comprises pre-operative planning as disclosed herein. For example, the pre-operative planning can comprise aligning an anterior edge of a glenoid implant with an anterior edge of a glenoid bone; adjusting a retroversion of the glenoid implant; adjusting an augmentation of the glenoid implant; adjusting an inferior tilt of the glenoid implant; evaluating bone support for the glenoid implant, wherein an amount of a rear surface of the glenoid implant that is supported by or touching bone is assessed; adjusting a medialization of the glenoid implant by assessing the volumetric amount of bone needed to be removed by reaming, or the minimum total distance of reaming necessary, in order to optimize the bone to implant interface; analyzing fixation support in the absence of central pegs that penetrate a vault medially; analyzing a joint line, comprising comparing an original joint line and a new joint line, wherein the new joint line is substantially similar to the original joint line; measuring and matching widths of the glenoid implant and the glenoid bone after reaming and aligning inferior and superior axes of the glenoid implant and bone; assessing and adjusting as needed a thickness/height of the glenoid implant; assessing and adjusting as needed a depth of a glenoid fossa; and assessing and adjusting as needed a thickness of a graft.

In some embodiments, methods of treating a patient, and/or surgical methods, are provided wherein one or more of the disclosed methods of analysis and optimization are performed on a patient in need of shoulder or other joint surgery. In some embodiments, methods of treating a patient are provided wherein a disclosed method of analysis and optimization is performed, an optimized guide is designed and created, and one or more glenoid and/or humeral implants are designed, created, and/or selected. In some embodiments, a method of treating a patient can comprise utilizing the pre-operative planning to design and optimize a guide and one or more glenoid and/or humeral implants, and the use of the guide to surgically implant the one or more glenoid and/or humeral prosthetic devices.

In some embodiments, a kit is provided wherein the kit can comprise a set of instructions for performing the disclosed pre-operative planning methods and analyses. Such a kit can further comprise one or more glenoid and/or humeral prosthetic devices, wherein the devices can be customizable or modular in design such that the prosthetic device can be optimized for the patient based on the pre-operative planning analysis. In some embodiments, a kit can further comprise a guide for placing a prosthetic device during shoulder surgery, wherein the guide can be optimized for the patient based on the pre-operative planning analysis. In some embodiments, a kit can further comprise a 3-D printing device for producing a guide and/or one or more glenoid and/or humeral prosthetic devices. In some embodiments, a kit can further comprise a computer-readable medium (software) for use in conducting the pre-operative planning, and designing a guide, glenoid implant and/or humeral implant based on input parameters gathered during the disclosed methods of analysis.

In some embodiments a patient can comprise a mammalian subject. In some embodiments, the patient can be a human subject, including an adult, adolescent or child.

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a" and "an" mean "one or more" when used in this application, including the claims.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a construct or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, "significance" or "significant" relates to a statistical analysis of the probability that there is a non-random association between two or more entities. To determine whether or not a relationship is "significant" or has "significance", statistical manipulations of the data can be performed to calculate a probability, expressed as a "p value". Those p values that fall below a user-defined cutoff point are regarded as significant. In some embodiments, a p value less than or equal to 0.05, in some embodiments less than 0.01, in some embodiments less than 0.005, and in some embodiments less than 0.001, are regarded as significant. Accordingly, a p value greater than or equal to 0.05 is considered not significant.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of designing a glenoid placement guide for use with pre-operative surgical planning, the method comprising:
   virtually aligning, with processing circuitry, an anterior edge of a glenoid implant with an anterior edge of a glenoid fossa of a scapula to determine alignment information;
   virtually adjusting, with the processing circuitry, one or more of a retroversion of the glenoid implant, an augmentation of the glenoid implant, or an inferior tilt of the glenoid implant to determine one or more of retroversion information, augmentation information, or inferior tilt information;
   virtually adjusting, with the processing circuitry, a medialization of the glenoid implant based on an assessment of a volumetric amount of the scapula needed to be removed or a minimum total distance of reaming for optimizing an interface between the glenoid implant and the glenoid fossa to determine medialization information;
   determining, with the processing circuitry, dimensions for one or more radial arms that extend from a hub of the glenoid placement guide based on the determined alignment information, one or more of the retroversion information, augmentation information, or inferior tilt information, and the medialization information;
   determining, with the processing circuitry, dimensions for one or more peripheral guide structures affixed to the one or more radial arms based on the determined alignment information, the medialization information, and one or more of the retroversion information, the augmentation information, or the inferior tilt information; and
   outputting, with the processing circuitry, information of the determined dimensions for the one or more radial arms and the determined dimensions for the one or more peripheral guide structures affixed to the one or more radial arms.

2. The method of claim 1, further comprising:
   virtually measuring, with the processing circuitry, and matching widths of the glenoid implant and the glenoid fossa after reaming and aligning inferior and superior axes of the glenoid implant and the glenoid fossa to determine widths of the glenoid implant and the glenoid fossa,
   wherein determining, with the processing circuitry, dimensions for the one or more radial arms comprises determining, with the processing circuitry, dimensions for the one or more radial arms based on the determined widths of the glenoid implant and the glenoid fossa.

3. The method of claim 1, wherein virtually aligning, virtually adjusting one or more of the retroversion of the glenoid implant, the augmentation of the glenoid implant, or the inferior tilt of the glenoid implant, and virtually adjusting the medialization comprises virtually aligning, virtually adjusting one or more of the retroversion of the glenoid implant, the augmentation of the glenoid implant, or the inferior tilt of the glenoid implant, and virtually adjusting, with the processing circuitry, the medialization based on pre-operative images.

4. The method of claim 1, further comprising determining, with the processing circuitry, a humeral implant, wherein determining, with the processing circuitry, the humeral implant comprises:
   determining a diameter of a humeral head;
   determining a height of the humeral head;
   determining a size of a humeral bone implant stem portion from Hounsfield units measured by computed tomography scan; and
   determining a best fit size of the humeral implant from a range of sizes based on the diameter of the humeral head, the height of the humeral head, and the size of the humeral bone implant stem portion, wherein the range of sizes is selected from the group consisting of length of stem, size of a humeral stem, diameter of stem, size diameter of head, height of head, and offset of a center spherical head compared to a center of a face of the humeral stem.

5. The method of claim 1, further comprising:
   comparing, with the processing circuitry, vectors in three dimensions, wherein the vectors comprise a distance and direction between tendon and muscle insertions on the scapula and a humerus of a patient, wherein the vectors measure the distance of relocation of humeral tuberosity compared to the scapula; and
   determining, with the processing circuitry, the glenoid implant based on comparison of the vectors.

6. The method of claim 1, further comprising:
   determining, with the processing circuitry, that the glenoid implant is a suitable glenoid implant based on:
      virtually conducting range of motion analysis, including virtually positioning a plurality of glenoid implants through ranges of motion; and
      measuring impact locations based on the virtual positioning of the glenoid implant.

7. The method of claim 1, further comprising:
determining, with the processing circuitry, that the glenoid implant is a suitable glenoid implant based on:
  virtually conducting soft tissue analysis comprising determining soft tissue insertion points; and
  measuring impact locations based on an implantation of the glenoid implant in the key soft tissue insertion points.

8. The method of claim 1, further comprising:
identifying, with the processing circuitry, an anchoring location on a surface of the glenoid fossa, wherein an anchoring pin channel is located on the hub and configured to guide an anchoring pin to the anchoring location on the surface of the glenoid fossa.

9. The method of claim 1, further comprising:
identifying, with the processing circuitry, a location on a surface of the glenoid fossa for placement of a depth-control pin, wherein the hub is configured to guide the depth-control pin to the location on the surface of the glenoid fossa.

10. The method of claim 1, further comprising:
manufacturing the glenoid placement guide based on the information of the determined dimensions for the one or more radial arms and the determined dimensions for the one or more peripheral guide structures affixed to the one or more radial arms.

* * * * *